US010953092B2

(12) United States Patent
Pai et al.

(10) Patent No.: US 10,953,092 B2
(45) Date of Patent: Mar. 23, 2021

(54) METHOD AND APPARATUS FOR PARTICLE ACTUATION IN A SPACE

(71) Applicant: California Institute of Technology, Pasadena, CA (US)

(72) Inventors: Alex H. Pai, Pasadena, CA (US); Seyed Ali Hajimiri, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 570 days.

(21) Appl. No.: 15/272,320

(22) Filed: Sep. 21, 2016

(65) Prior Publication Data

US 2017/0263363 A1 Sep. 14, 2017

Related U.S. Application Data

(60) Provisional application No. 62/222,104, filed on Sep. 22, 2015, provisional application No. 62/335,974, filed on May 13, 2016.

(51) Int. Cl.
*A61K 41/00* (2020.01)
*A61K 9/50* (2006.01)
*H01F 7/02* (2006.01)

(52) U.S. Cl.
CPC ........... *A61K 41/00* (2013.01); *A61K 9/5094* (2013.01); *H01F 7/0278* (2013.01)

(58) Field of Classification Search
CPC ...... A61K 41/00; A61K 9/5094; H01F 7/0278
See application file for complete search history.

(56) References Cited

U.S. PATENT DOCUMENTS 5,681,478 A * 10/1997 Lea ................ B03C 1/288
 210/222
6,312,910 B1 * 11/2001 Vellinger ............ C07K 1/24
 435/6.13

(Continued)

OTHER PUBLICATIONS

"Cernak,J.; Helgesen,G. Aggregation of magnetic holes in a rotating magnetic field, 2008, Phys. Rev. E 78, 061401" (Year: 2008).*

(Continued)

*Primary Examiner* — Scott Bauer
(74) *Attorney, Agent, or Firm* — Alston & Bird LLP

(57) ABSTRACT

A device is dynamically programmable to generate at least a first magnetic field during a first time interval, and at least a second magnetic field during a second time interval thereby causing the particles exposed to the change in the magnetic field to aggregate to a target region. The device is further dynamically programmable to switch between the first and second magnetic fields for any number of cycles. Optionally, the device includes a multitude of conductors that receive a first current during the first time interval to generate the magnetic field, and a second multitude of conductors that receive a second current during the second time interval to generate the second magnetic field. The second multitude of conductors may be substantially parallel to the first multitude of conductors. A controller disposed within the device is adapted to vary the frequency of switching between the first and second magnetic fields.

33 Claims, 25 Drawing Sheets
(7 of 25 Drawing Sheet(s) Filed in Color)

(56) References Cited

U.S. PATENT DOCUMENTS

2008/0014442 A1* 1/2008 Rida .................. G01N 33/5434
428/403
2014/0227679 A1* 8/2014 Lee .......................... B03C 1/01
435/5

OTHER PUBLICATIONS

Alizadeh, et al., "Tumor-Associated Macrophages Are Predominant Carriers of Cyclodextrin-Based Nanoparticles into Gliomas," *Nanomedicine,* 6(2):382-390, (2010).

Smith, et al., "Direct Mechanical Measurements of the Elasticity of Single DNA Molecules by Using Magnetic Beads," *Science,* 258(5085):1122-1126, (1992).

Molday, et al., "Immunospecific Ferromagnetic Iron-Dextran Reagents for the Labeling and Magnetic Separation of Cells," *Journal of Immunological Methods,* 52:353-367, (1982).

Ito, et al., "Tissue Engineering Using Magnetite Nanoparticles and Magnetic Force: Heterotypic Layers of Cocultured Hepatocytes and Endothelial Cells," *Tissue Engineering,* 10(5-6):833-840, (2004).

Suwa, et al., "Magnetoanalysis of micro/nanoparticles: A review," *Analytica Chimica Acta,* 690:137-147, (2011).

\* cited by examiner

METHOD AND APPARATUS FOR PARTICLE ACTUATION IN A SPACE

CROSS REFERENCE TO RELATED APPLICATIONS

The present application claims benefit under 35 USC 119(e) of Application Ser. No. 62/222,104, filed Sep. 22, 2015, and Application Ser. No. 62/335,974, filed May 13, 2016, the contents of both of which are incorporated herein by reference in their entirety.

STATEMENT OF FEDERAL FUNDING

The present invention was made with government support under Grant No. NS081594, awarded by the National Institutes of Health. The government has certain rights in the invention.

FIELD OF THE INVENTION

The present invention relates to controlled movement and aggregation of particles, particularly using magnetic or electric fields.

BACKGROUND OF THE INVENTION

Particles may be moved mechanically, or by application of electric or magnetic fields or fluidic energy. Magnetic particle manipulation using magnetic tweezers is known to have been used in cell separation and tissue engineering. However, such system, among other disadvantages are costly, require complicated setups, have small active areas, are not scalable, and difficult to image.

Traditional tumor treatment therapies, such as surgery, chemotherapy, and radiation therapy, damage peripheral tissue and are ineffective in treating privileged organs such as the brain and central nervous system. Immunotherapy, utilizing functionalized nanoparticles, has been shown to be a promising treatment for intracranial gliomas, which is the most common type of malignant brain tumor. However, the retention and delivery of immune cells and nanoparticles to the tumor site remains a challenge.

Particle movement and aggregation is important in a number of applications as it allows for delivery of cargo to a point in space. The cargo may be different depending on the desired application. For example, cancer immunotherapy can be greatly enhanced through the delivery of adjuvants directly to the tumor site. In tissue engineering, the particles may be used to transport stem cells to a desired location to form more complex cellular structures. In the medical diagnostics industry, the particles may be coated with reporter molecules and traversed through a collection of points in a biological sample for determining the presence of a target. Such particles may also be coated with capture molecules to gather a sample.

The particles may be used to induce flow or vortices inside a medium. The size of such particles may vary greatly depending on the application. In transporting the particles from one location to another, a feedback method is typically used to track the particle's position. This allows the particle to be steered toward a location when a stable aggregation point cannot be achieved. Tracking a particle's position using a feedback loop adds to the cost and complexity of the systems.

BRIEF SUMMARY OF THE INVENTION

A method of aggregating particles, in accordance with one embodiment of the present invention includes, in part, generating at least a first magnetic field during a first time interval, and generating at least a second magnetic field during a second time interval thereby causing the particles exposed to the first and second magnetic fields to aggregate to a target region in response to the change from the first magnetic field to the second magnetic field. In one embodiment, the method further includes, in part, switching between the at least first and second magnetic fields for a multitude of cycles thereby to aggregate the particles in the target region.

In one embodiment, the first magnetic field is generated by passing a first current through a first multitude of conductors during the first time interval, and the second magnetic field is generated by passing a second current through a second multitude of conductors during the second time interval. In one embodiment, the first and second magnetic fields are generated in response to moving permanent magnets. In one embodiment, the first and second magnetic fields are generated in response to changes in the magnetization orientation of a Ferro-magnetic material.

In one embodiment, the second multitude of conductors are substantially parallel to the first multitude of conductors. In one embodiment, the first and second time intervals are non-overlapping time intervals. In one embodiment, at least a subset of the first multitude of conductors are disposed in the second multitude of conductors. In one embodiment, at least a portion of the first and second time intervals occur during N cycles of a clock signal, where N is an integer greater than one. In one embodiment, the portion of the first time interval is defined by N high values of the clock and the portion of the second time interval is defined by N low values of the clock.

In one embodiment, the method further includes, in part, varying the frequency of the switching between the first and second magnetic fields. In one embodiment, the method further includes, in part, varying the first and second currents. In one embodiment, the frequency of switching between the magnetic fields is selected in accordance with a friction coefficient of the particles. In one embodiment, the frequency is selected in accordance with a drag coefficient of the particles. In one embodiment, the frequency is selected in accordance with a mass of the particles. In one embodiment, the first current is equal to the second current. In one embodiment, the method further includes, generating the first and second magnetic fields using an open loop system. In one embodiment, the first time interval is substantially equal to the second time interval. In one embodiment, the first and second magnetic fields are generated by a multitude of magnetic field generating components adapted to mate with one another to form a mesh conforming to contours of a surface enclosing the region in which the particles are disposed. In one embodiment, the second multitude of conductors are formed by rotating the first multitude of conductors.

A dynamically programmable device adapted to aggregate particles, in accordance with one embodiment of the present invention, in part, generates at least a first magnetic field during a first time interval, and at least a second magnetic field during a second time interval thereby to cause the particles to aggregate to a target region in response to the change from the first magnetic field to the second magnetic field. In one embodiment, the device is further dynamically programmable to switch between the first and second magnetic fields for a multitude of cycles thereby to aggregate the particles in the target region.

In one embodiment, the device includes, in part, a first multitude of conductors adapted to receive a first current during the first time interval to generate the first magnetic field, and a second multitude of conductors adapted to receive a second current during the second time interval to generate the second magnetic field. In one embodiment, the device further includes, in part, at least one permanent magnet, and a controller adapted to move the permanent magnet to generate the at least first and second magnetic fields. In one embodiment, the device includes, in part, a Ferro-magnetic material, and a controller adapted to change the magnetization orientation of the Ferro-magnetic material thereby to generate the first and second magnetic fields.

In one embodiment, the second multitude of conductors are substantially parallel to the first multitude of conductors. In one embodiment, the first and second time intervals are non-overlapping time intervals. In one embodiment, at least a subset of the first multitude of conductors are disposed in the second multitude of conductors. In one embodiment, at least a portion of the first and second time intervals occur during N cycles of a clock signal. In one embodiment, such portion of the first time interval is defined by N high values of the clock, and such portion of the second time interval is defined by N low values of the clock.

In one embodiment, the device further includes, in part, a controller adapted to vary the frequency of the switching between the first and second magnetic fields. In one embodiment, the device further includes, in part, a controller adapted to vary the first and second currents. In one embodiment, the controller is further adapted to select the frequency of switching between the first and second magnetic fields in accordance with a friction coefficient of the particles. In one embodiment, the controller is further adapted to select the frequency of switching between the first and second magnetic fields in accordance with a drag coefficient of the particles. In one embodiment, the controller is further adapted to select the frequency of switching between the first and second magnetic fields in accordance with a mass of the particles.

In one embodiment, the first current is equal to the second current. In one embodiment, the device is an open loop device and uses no feedback loop. In one embodiment, the first time interval is substantially equal to the second time interval. In one embodiment, the device further includes, in part, a multitude of magnetic field generating components adapted to mate with one another to form a mesh conforming to contours of a surface enclosing a region in which the particles are disposed. In one embodiment, the second multitude of conductors are formed by rotating the first multitude of conductors.

A device, in accordance with one embodiment of the present invention, includes, in part, a first multitude of conductors disposed along a first axis, a second multitude of conductors disposed along the first axis and having positions defined by a rotation of the first multitude of conductors, a third multitude of conductors disposed along a second axis, a fourth multitude of conductors disposed along the second axis and having positions defined by a rotation of the third plurality of conductors. The device further includes a control circuit adapted to: supply a first current to each of the first multitude of conductors during N high values of a clock, supply a second current to each of the second multitude of conductors during the N low values of the clock, supply a third current to each of the third multitude of conductors during M high values of the clock following the termination of the N cycles of the clock, and supply a fourth current to each of the fourth multitude of conductors during the M low cycles values of the clock following the termination of the N cycles of the clock.

In one embodiment, the first, second, third and fourth currents have substantially similar magnitudes. In one embodiment, the high values of the clock cover a time period substantially equal to a time period covered by the low values of the clock. In one embodiment, the first axis is substantially perpendicular to the second axis. In one embodiment, the device is further adapted to vary N or M. In one embodiment, the number of conductors in the first multitude of conductors is equal to the number of conductors in the second multitude of conductors.

A method of aggregating particles, in accordance with one embodiment of the present invention, includes, in part, supplying a first current to each of a first multitude of conductors during N high values of a clock, supplying a second current to each of a second multitude of conductors during the N low values of the clock, supplying a third current to each of a third multitude of conductors during M high values of the clock following the termination of the N cycles of the clock, and supplying a fourth current to each of the fourth multitude of conductors during the M low values of the clock following the termination of the N cycles of the clock.

In one embodiment, the second multitude of conductors have positions defined by one or more rotations of the first multitude of conductors. In one embodiment, the fourth multitude of conductors have position defined by one or more rotations of the third multitude of conductors. In one embodiment, the first and second multitude of conductors are positioned along a first axis. In one embodiment, the third and fourth multitude of conductors are positioned along a second axis. In one embodiment, the second axis is substantially perpendicular to the first axis.

In one embodiment, the first, second, third and fourth currents have substantially similar magnitudes. In one embodiment, the high values of the clock cover a time period substantially equal to a time period covered by the low values of the clock. In one embodiment, the number of conductors in the first multitude of conductors is equal to the number of conductors in the second multitude of conductors.

A method of aggregating particles, in accordance with one embodiment of the present invention, includes in part, generating a first magnetic field during each of N low values of a clock signal. The first magnetic field has a profile that is equivalent to a field profile generated when a first current is supplied to each of a first multitude of conductors. The method further includes, in part, generating a second magnetic field during high values of at least a subset of the N cycles of the clock signal. The second magnetic field has a profile that is equivalent to a field profile generated when a second current is supplied to each of a second multitude of conductors.

A method of aggregating particles, in accordance with one embodiment of the present invention, includes in part, generating a first magnetic field during each of N low values of a clock signal. The first magnetic field has a profile that is equivalent to a field profile generated when a first current is supplied to each of a first multitude of conductors positioned along a first direction. The method further includes, in part, generating a second magnetic field during high values of at least a subset of the N cycles of the clock signal. The second magnetic field has a field profile equivalent to a field profile generated when a second current is supplied to each of a second multitude of conductors positioned along a second direction. The method further includes, in part, generating a third magnetic field during each of K low values of the clock signal. The third magnetic field has a field profile that is equivalent to a field profile generated when a third current is supplied to each of a third multitude of conductors positioned along a third direction. The method further includes, in part, generating a fourth magnetic field during high values of at least a subset of the K cycles of the clock signal. The fourth magnetic field has a field profile that is equivalent to a field profile generated when a fourth current is supplied to each of a fourth multitude of conductor positioned along a fourth direction.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1A:
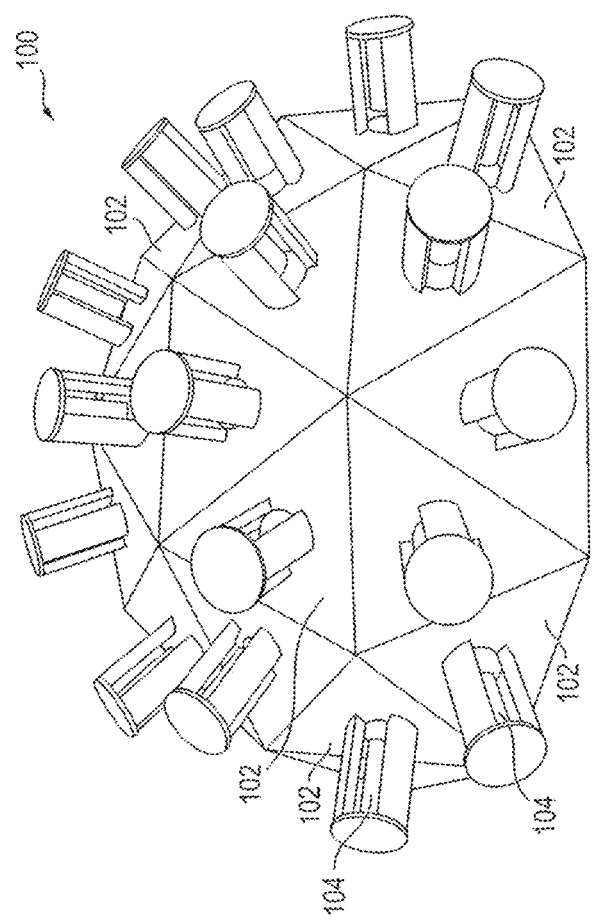
FIG. 1A shows an exemplary device adapted to aggregate magnetic particles in a target region, in accordance with one exemplary embodiment of the present invention.

Figure B is a simplified block diagram of an actuation block disposed in the device of FIG. 1A.

Figure 1B:
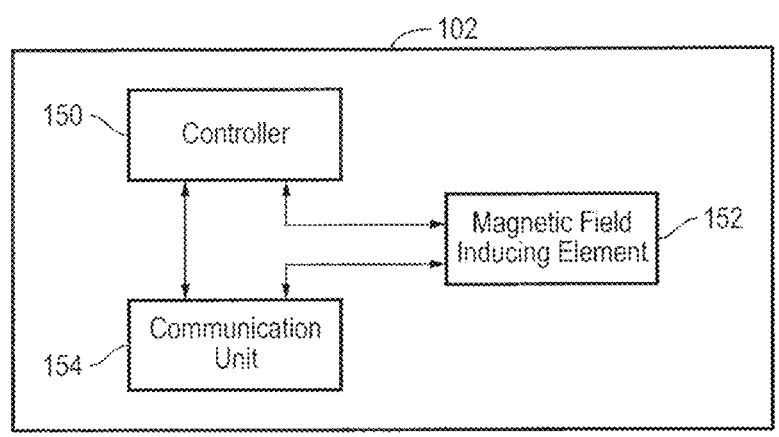
Figure 1C:
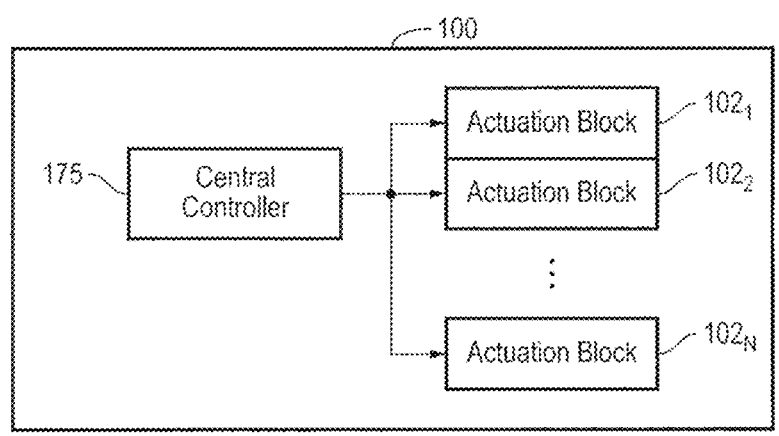

FIG. 1C is a simplified block diagram of the device shown in FIG. 1, in accordance with one exemplary embodiment of the present invention.

Figure 2A:
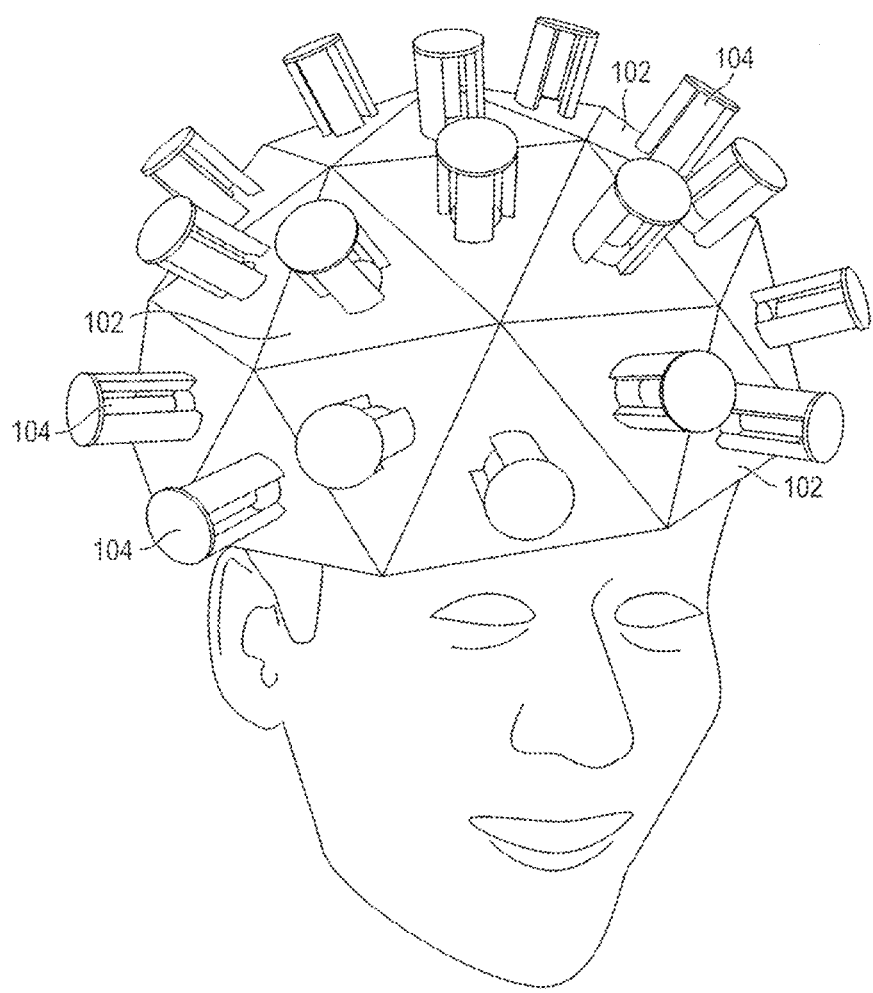

FIG. 2A shows the device of FIG. 1 when positioned over a person's head.

Figure 2B:
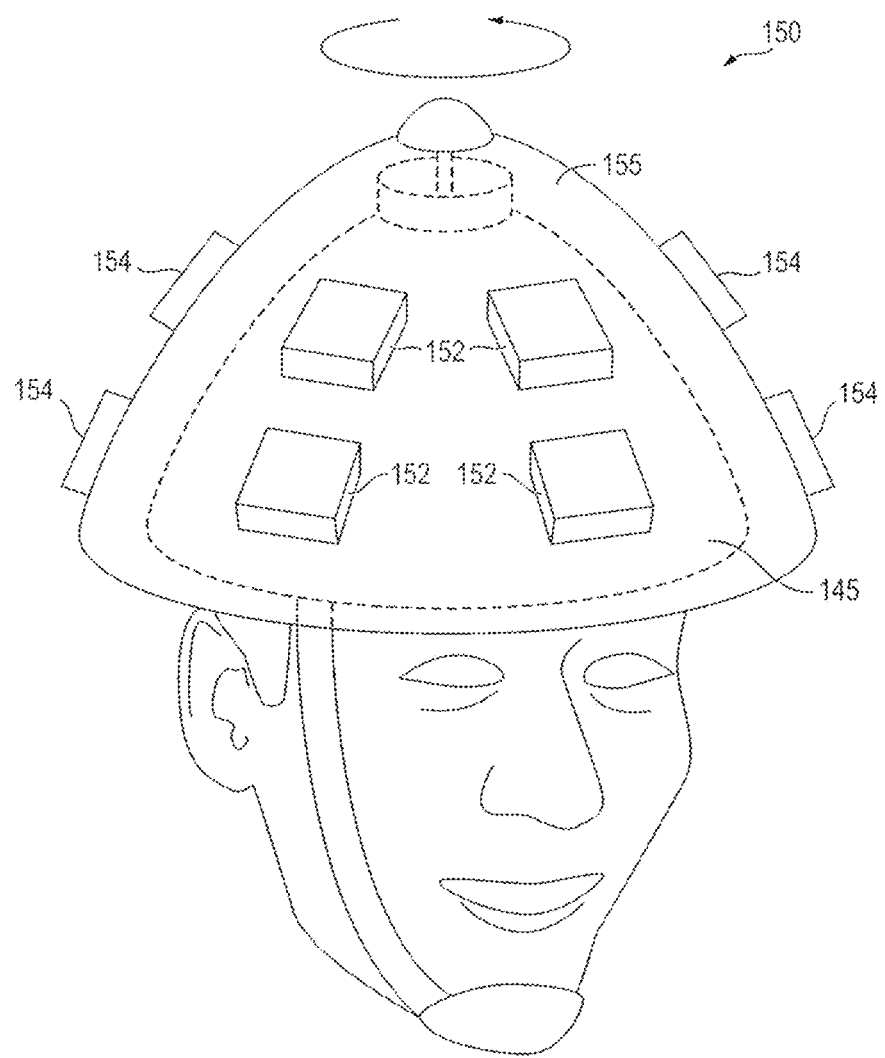

FIG. 2B shows an exemplary device adapted to aggregate magnetic particles in a target region, in accordance with another exemplary embodiment of the present invention.

Figure 3:
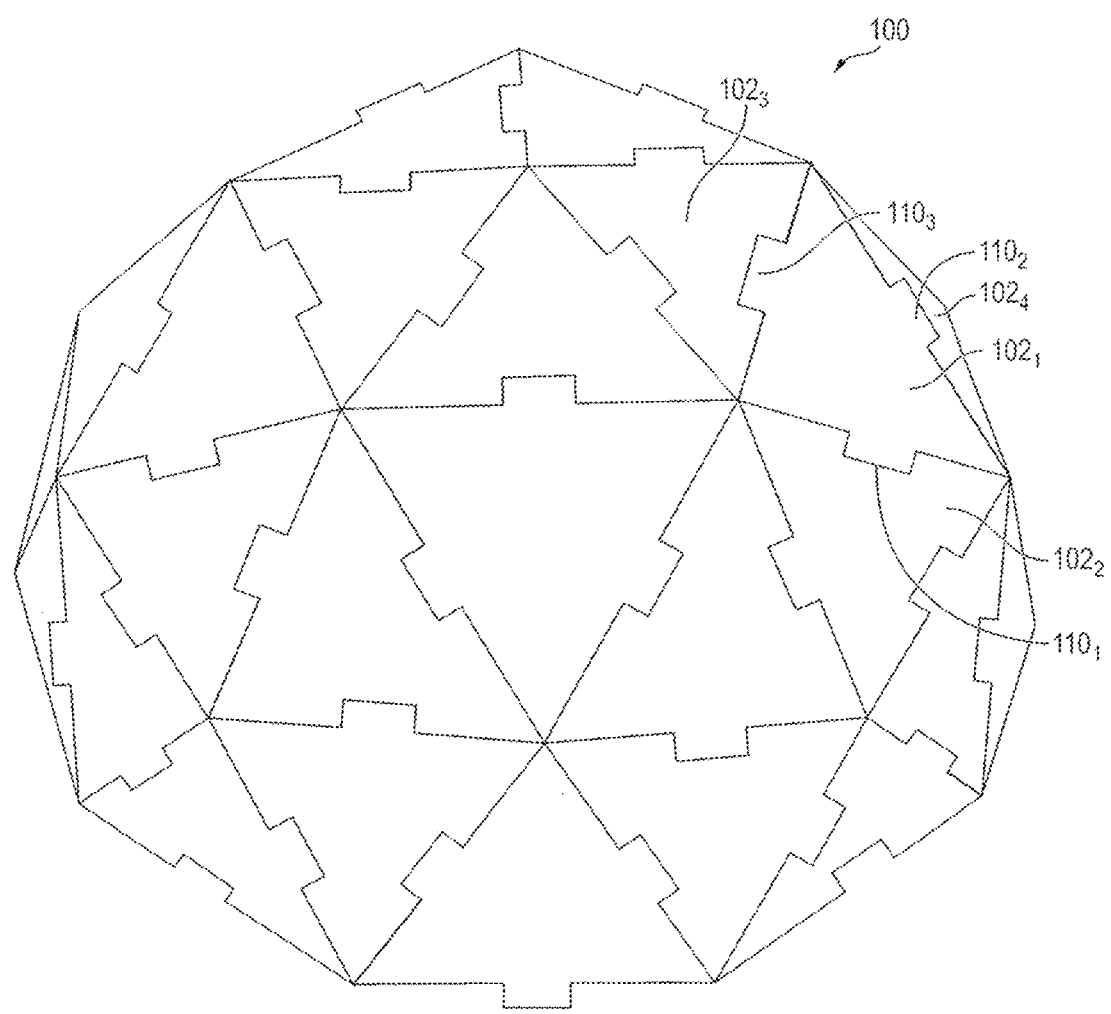

FIG. 3 is a simplified view of a multitude of components coupled to one another to form a device, in accordance with one exemplary embodiment of the present invention.

Figure 4:
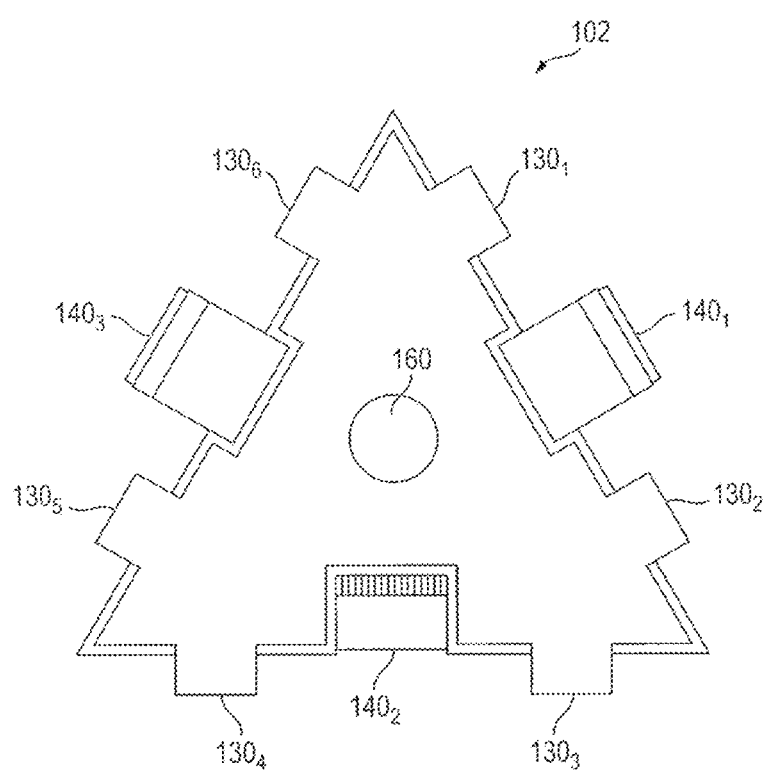

FIG. 4 is a more detailed view of a component used in forming the device of FIG. 3, in accordance with one exemplary embodiment of the present invention.

Figure 5:
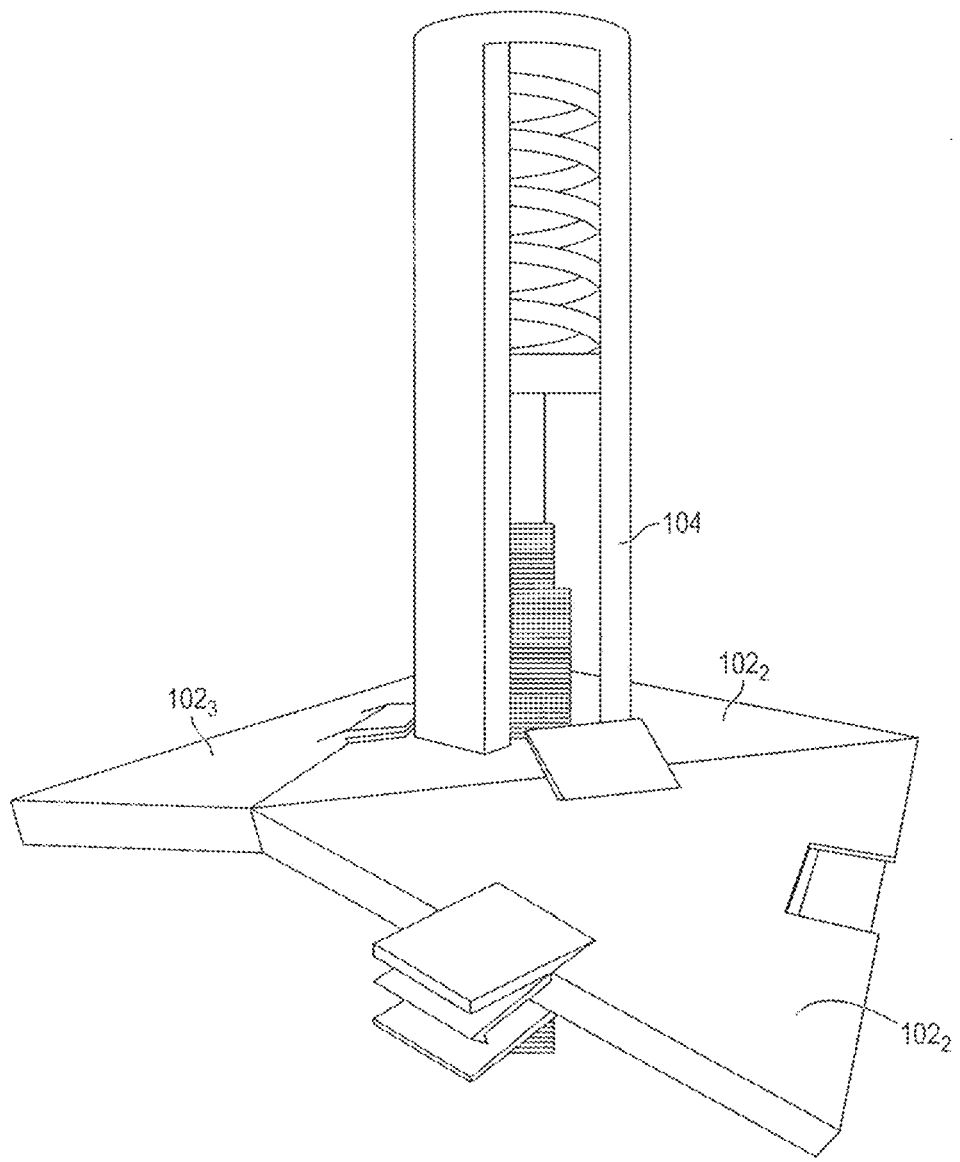

FIG. 5 shows a number of components coupled together to form a device having disposed therein a magnetic field inducing element, in accordance with another embodiment of the present invention.

Figure 6A:
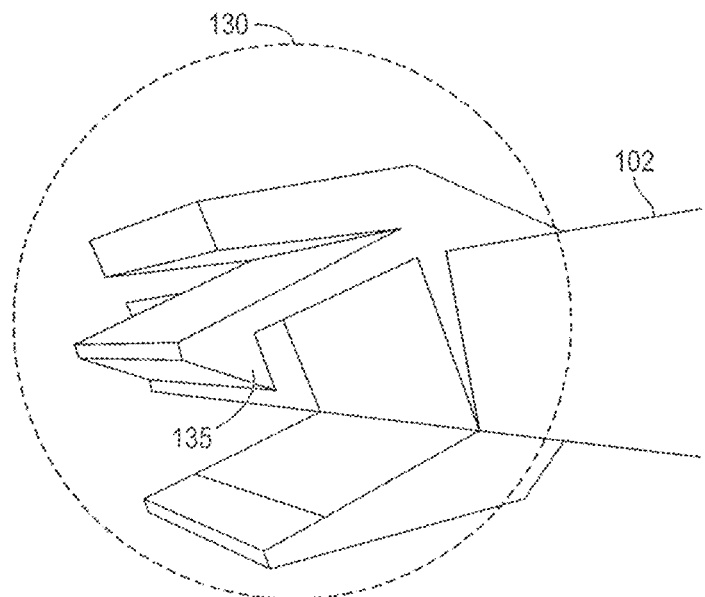
Figure 6B:
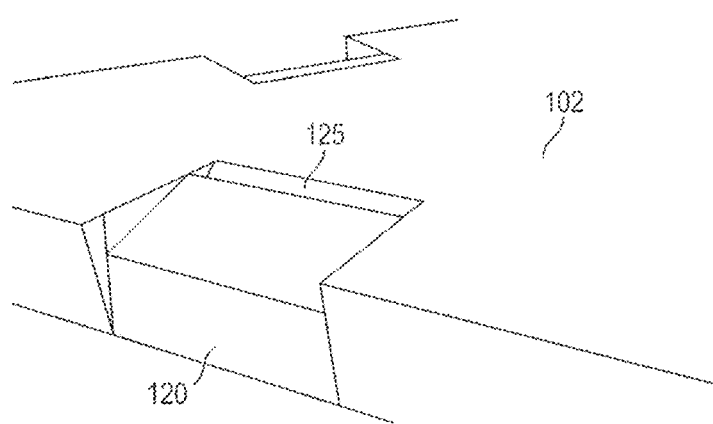

FIGS. 6A and 6B are perspective side views of a component disposed in the device of FIG. 1, in accordance with one exemplary embodiment of the present invention.

Figure 7:
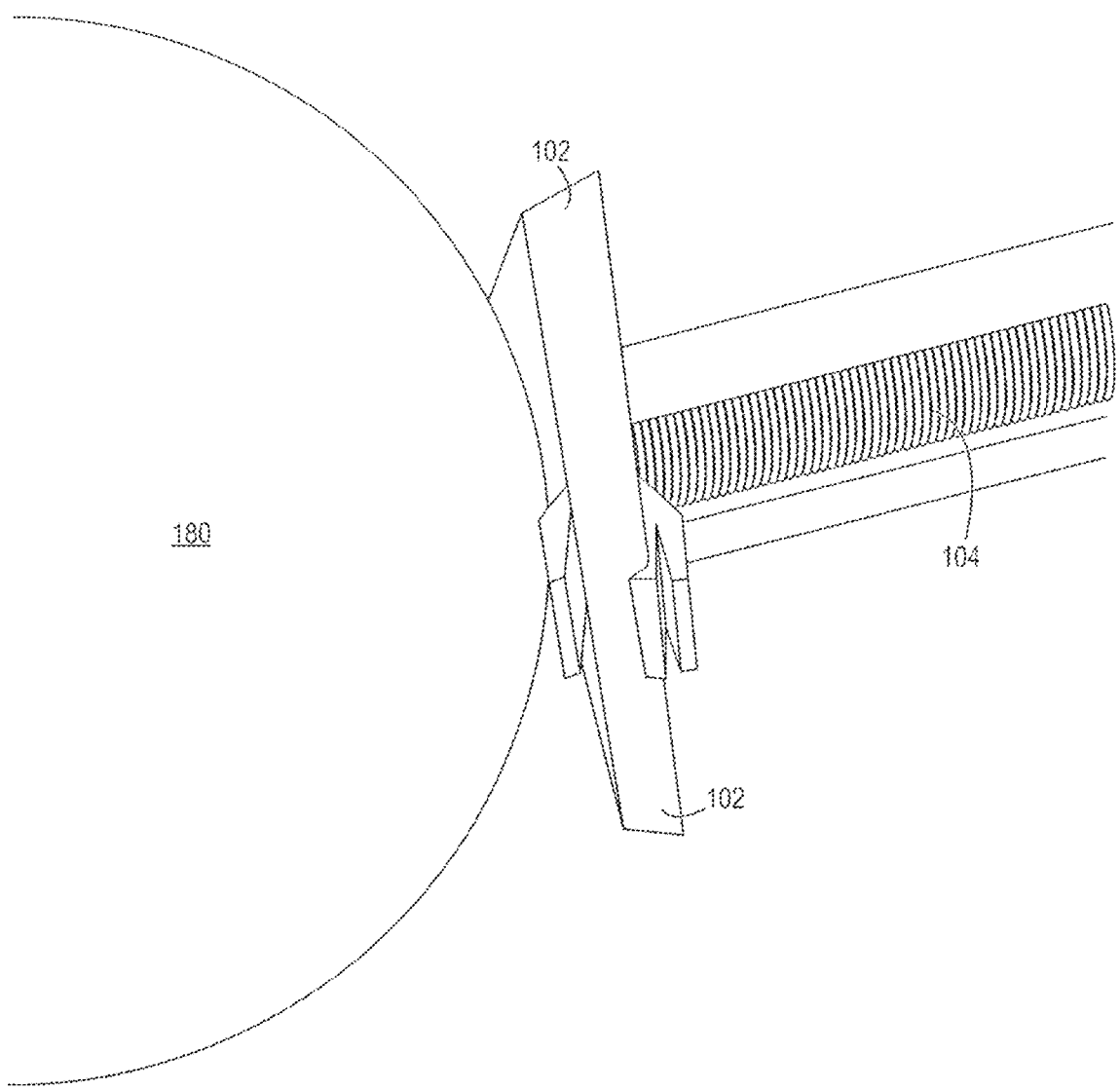

FIG. 7 is a side view of a portion of the device of FIG. 1 placed in proximity of an spherical object to control the movement of magnetic particles therein, in accordance with one embodiment of the present invention.

Figure 8B:
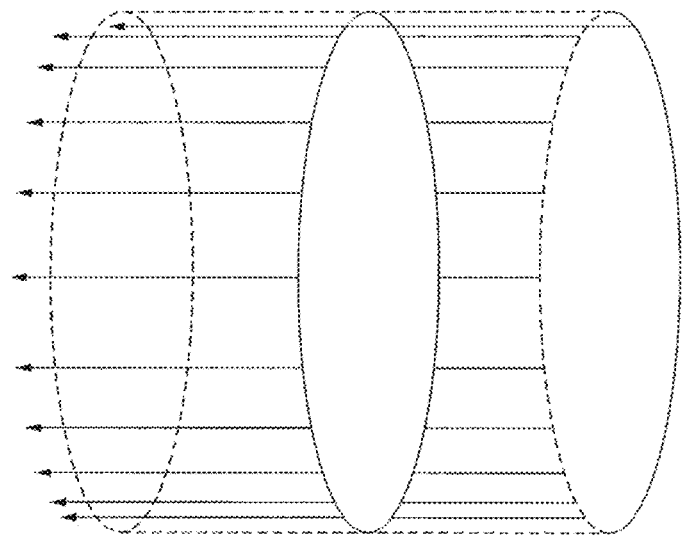
Figure 8A:
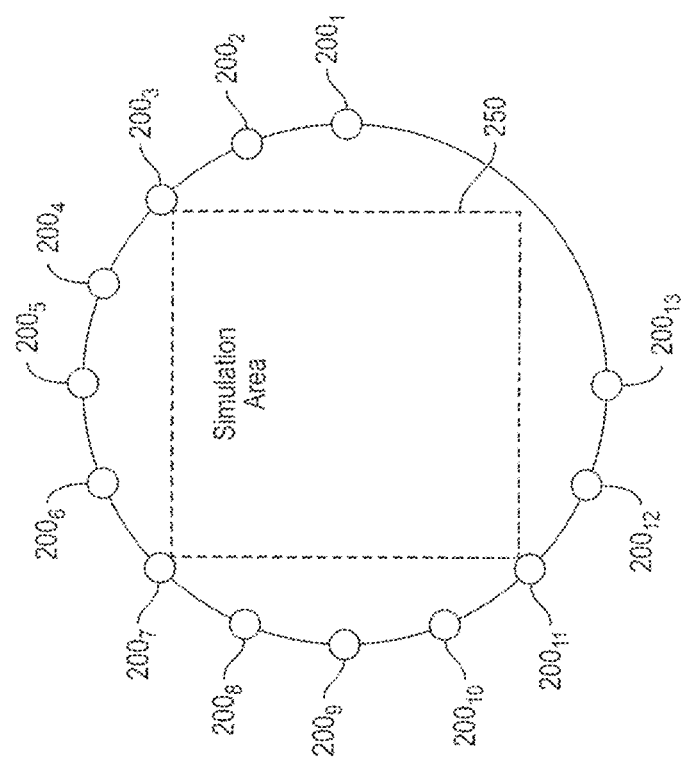

FIG. 8A is a top view of a circular area that a device, in accordance with one exemplary embodiment of the present invention, may enclose to control the movement of and aggregate magnetic particles thereon.

FIG. 8B is a perspective side view of the arrangement shown in FIG. 8A.

Figure 9A:
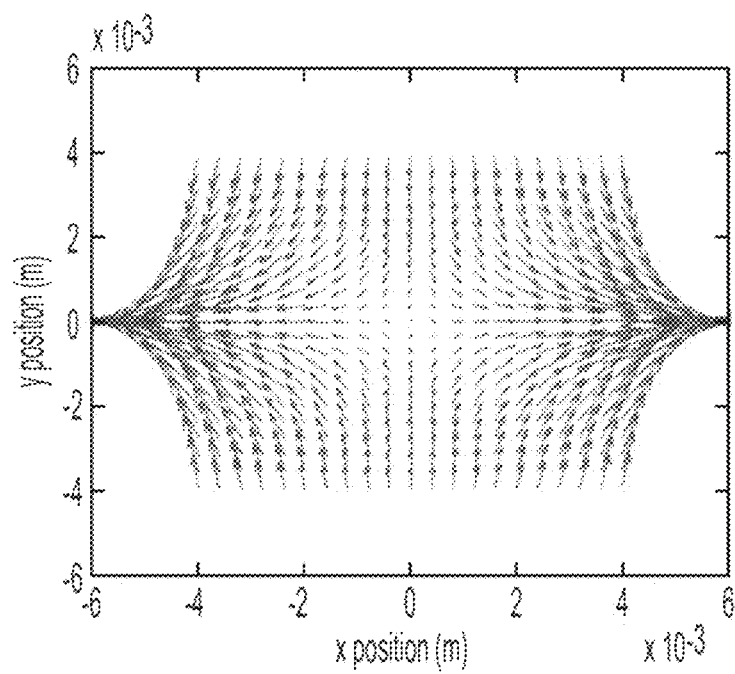
Figure 9B:
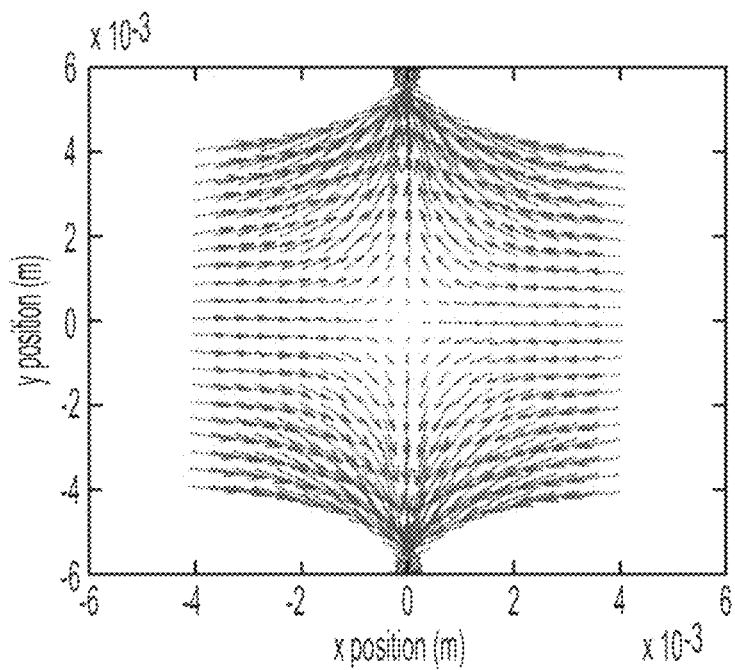

FIGS. 9A and 9B are exemplary quiver plots of the magnetic field profiles that a device, in accordance with one embodiment of the present invention, is adapted to generate.

Figure 10A:
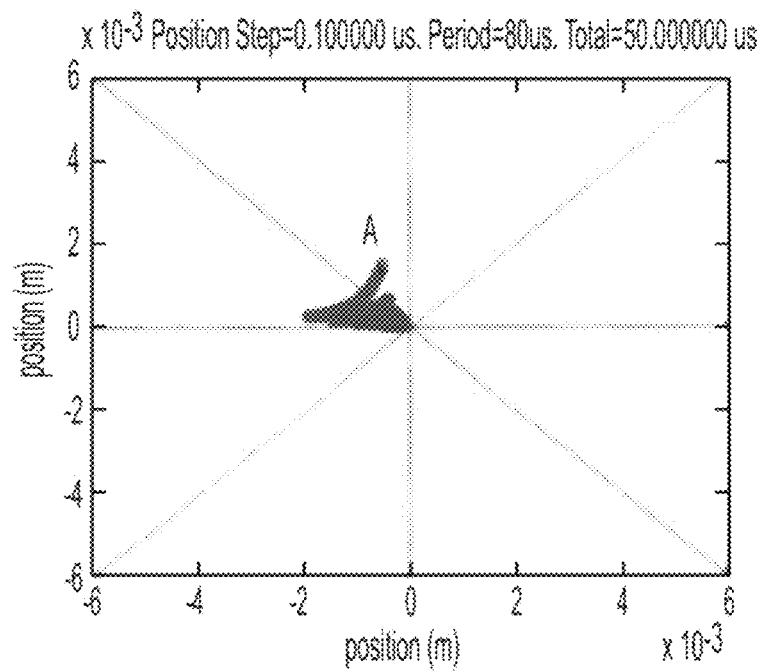

FIG. 10A shows the trajectory of particles subjected to the magnetic field profiles shown in FIGS. 9A and 9B, in accordance with one exemplary embodiment of the present invention.

Figure 10B:
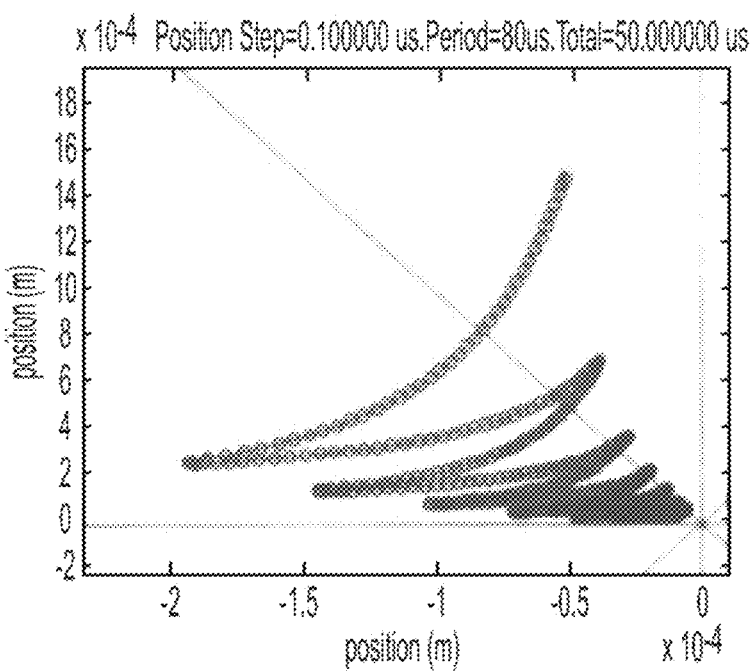

FIG. 10B is an expanded view of the trajectory of the particles shown in FIG. 10A.

Figure 11A:
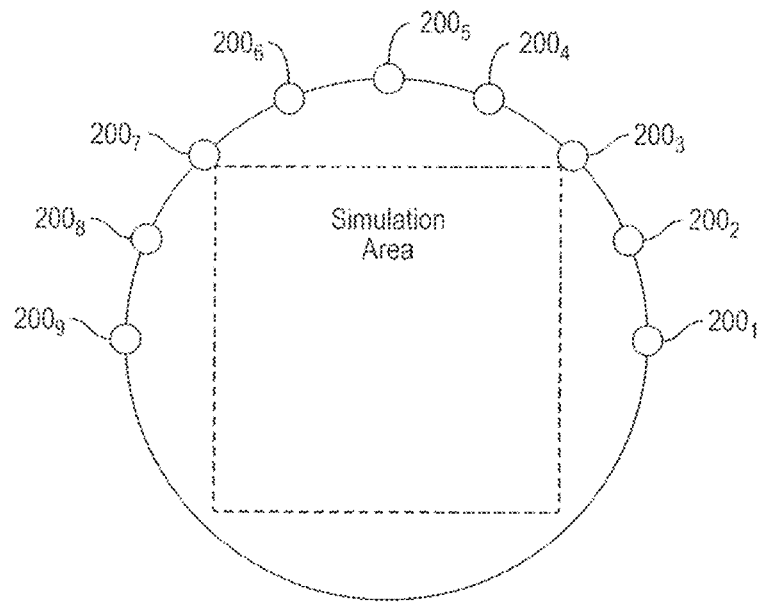
Figure 11B:
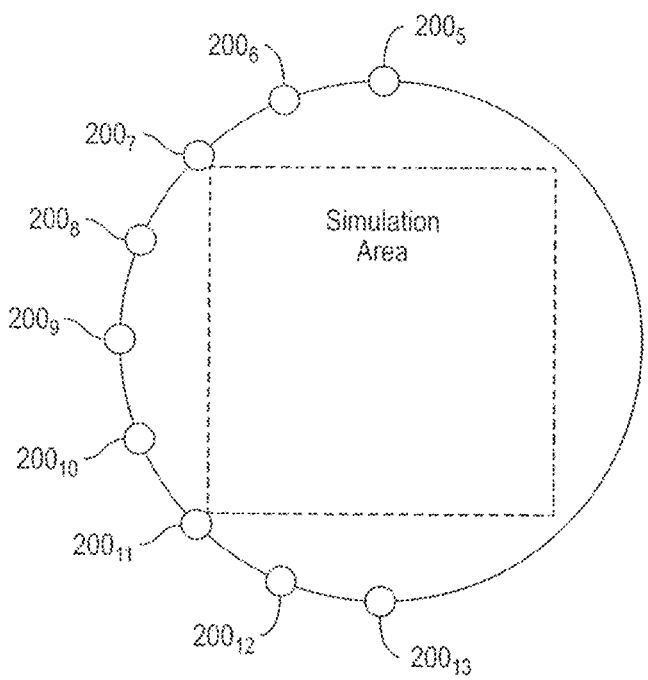

FIGS. 11A and 11B are simplified top views of different positions of a multitude of magnetic field inducing elements adapted to create changing magnetic field profiles within a circular region they enclose, in accordance with one exemplary embodiment of the present invention.

FIGS. 12A and 12C-12E show the speed distribution of particles in response to the change in the frequency of switching between the magnetic field profiles shown in FIGS. 9A and 9B, in accordance with one exemplary embodiment of the present invention.

Figure 12A:
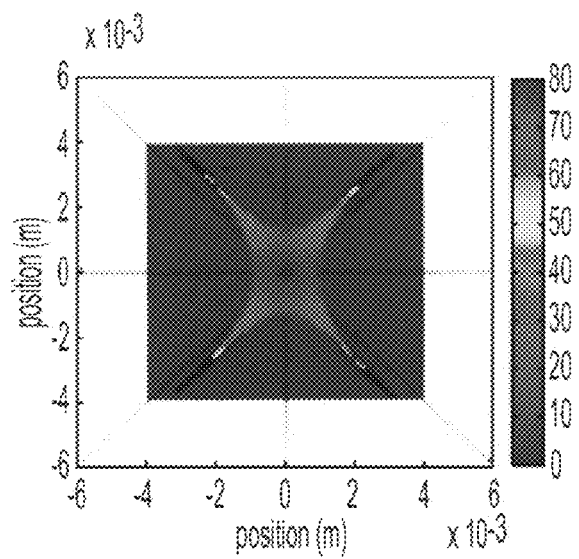
Figure 12C:
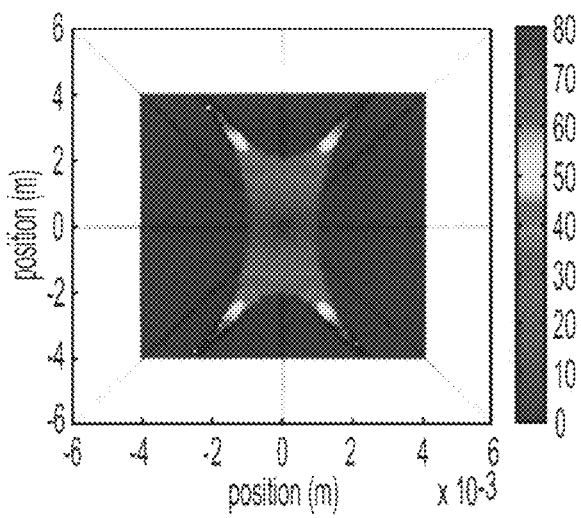
Figure 12D:
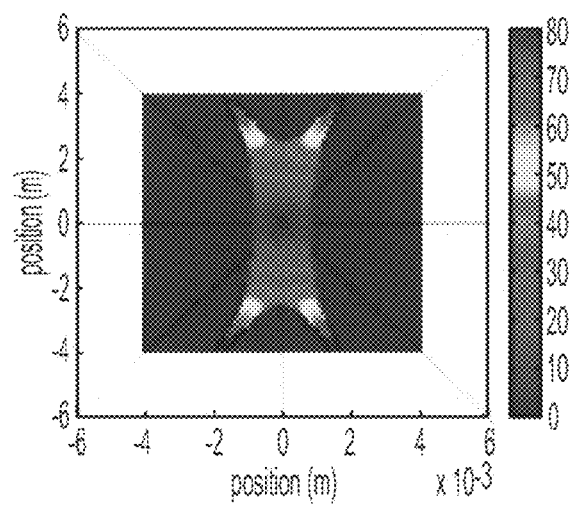
Figure 12E:
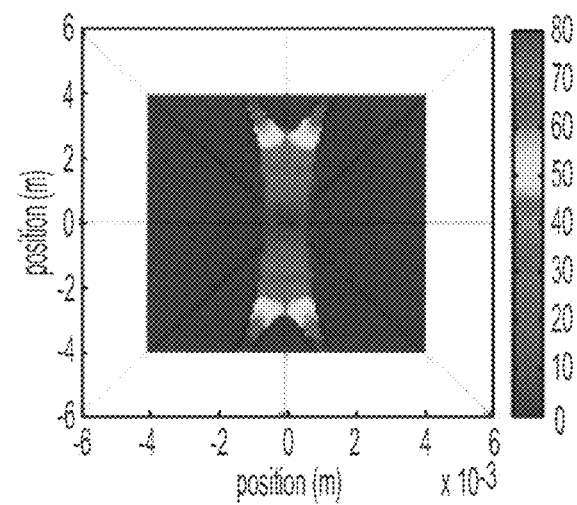
Figure 12B:
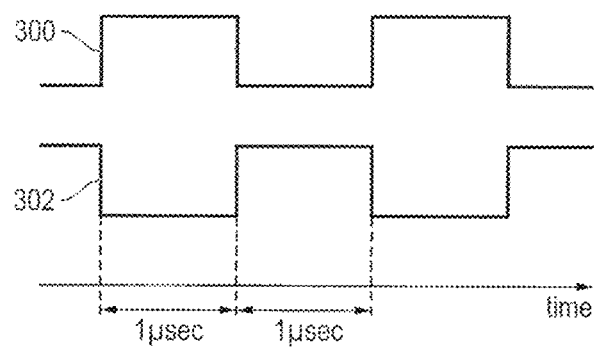

FIG. 12B is an exemplary timing diagram of signals applied to generate the magnetic field profiles shown in FIG. 12A.

Figure 13A:
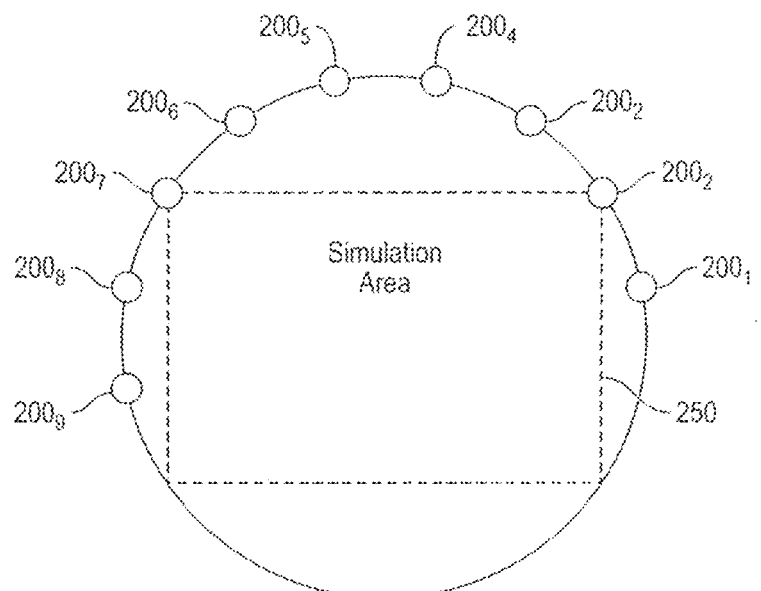
Figure 13B:
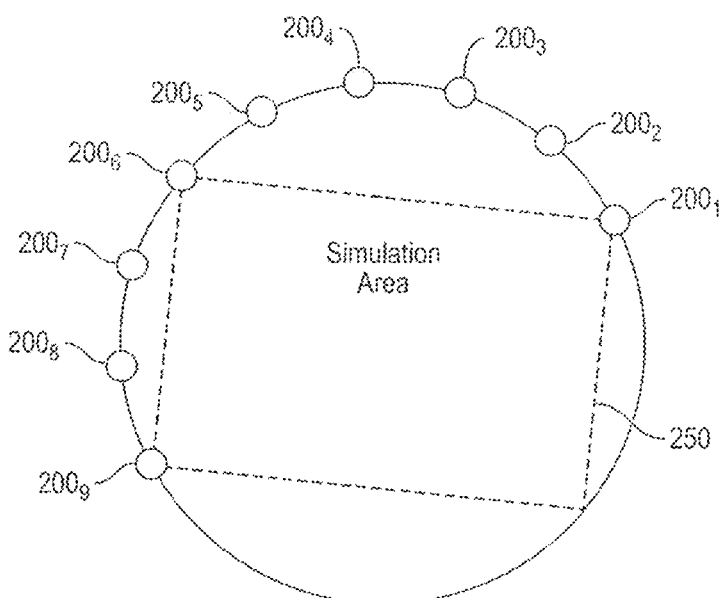

FIGS. 13A and 13B show positions of the magnetic field inducing elements of FIG. 11A after a number of counter clockwise rotations, in accordance with one exemplary embodiment of the present invention.

FIGS. 14A-14D show the speed distribution of magnetic particles positioned within the circular area shown in FIG. 1A, in response to the change in the frequency of the alternating magnetic fields, in accordance with one embodiment of the present invention.

Figure 15:
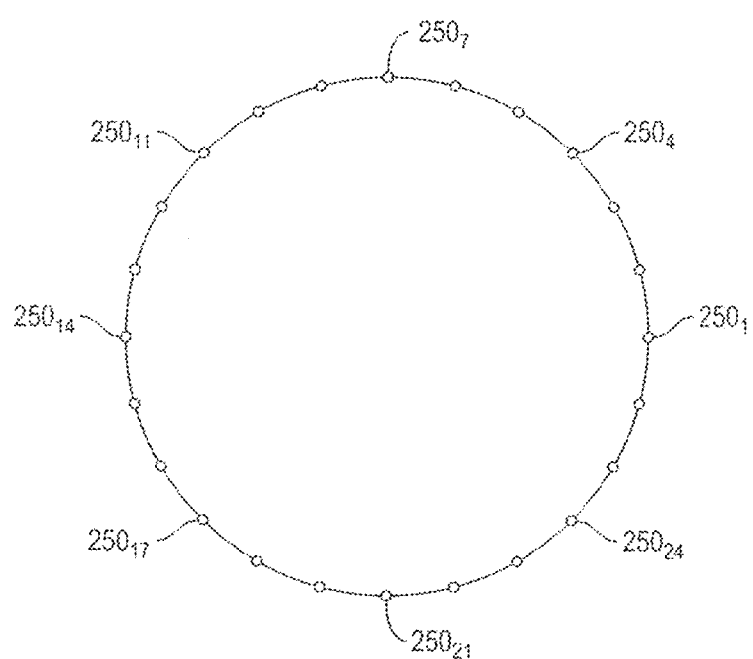

FIG. 15 is a simplified top views of different positions of a multitude of magnetic field inducing elements adapted to create changing magnetic field profiles within a circular region they enclose, in accordance with one exemplary embodiment of the present invention.

Figure 16A:
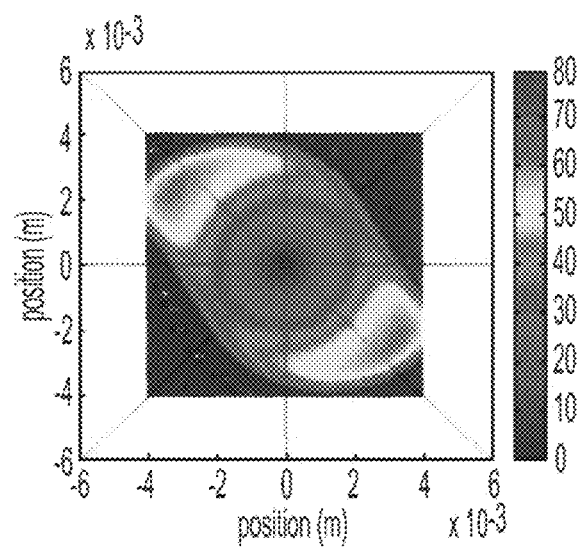

FIG. 16A shows the speed distribution of the magnetic particles at room temperature positioned within the simulation area of FIG. 13A.

Figure 16B:
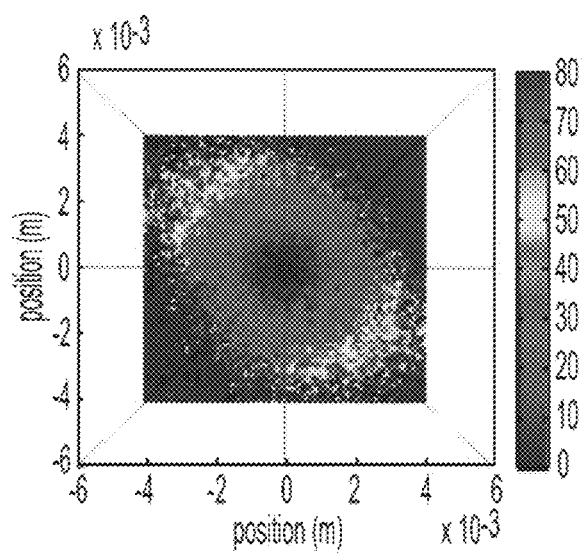
Figure 16C:
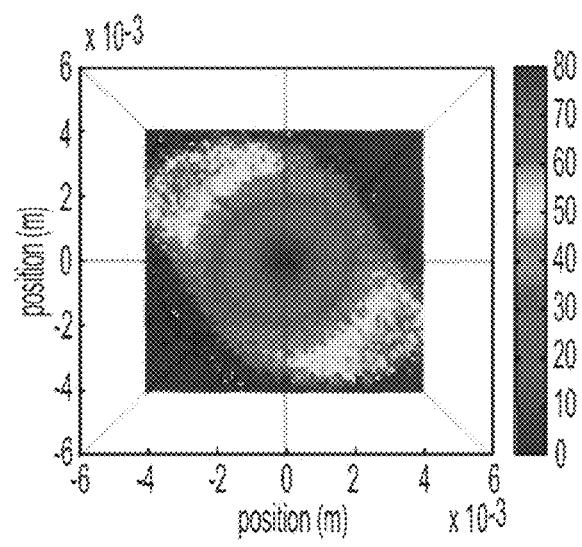
Figure 16D:
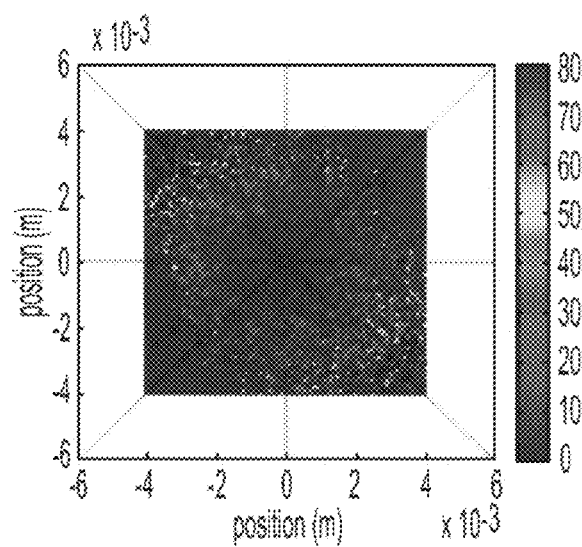

FIGS. 16B, 16C and 16D show the speed distribution of the particles of FIG. 16A when the Brownian motion is increased by factors of $10^{10}$, $10^{11}$ and $10^{12}$ respectively.

Figure 17B:
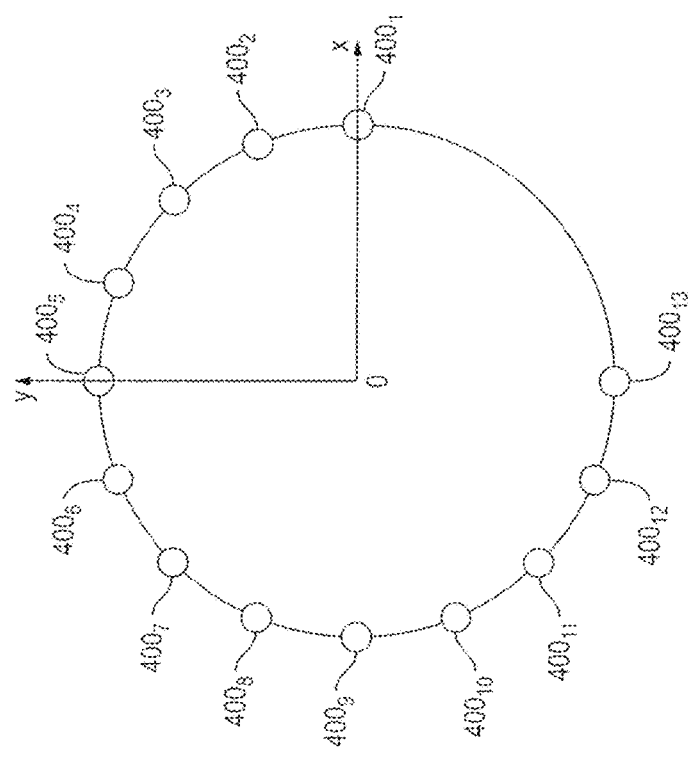
Figure 17C:
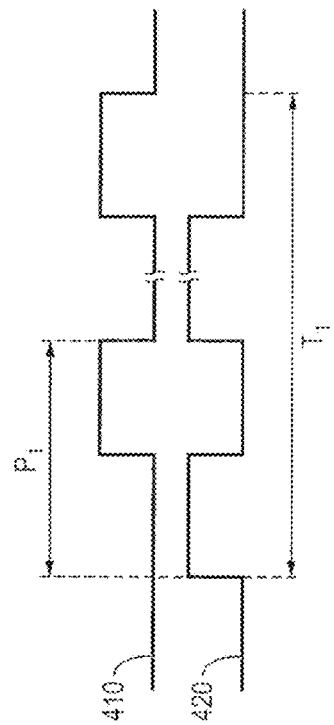
Figure 17A:
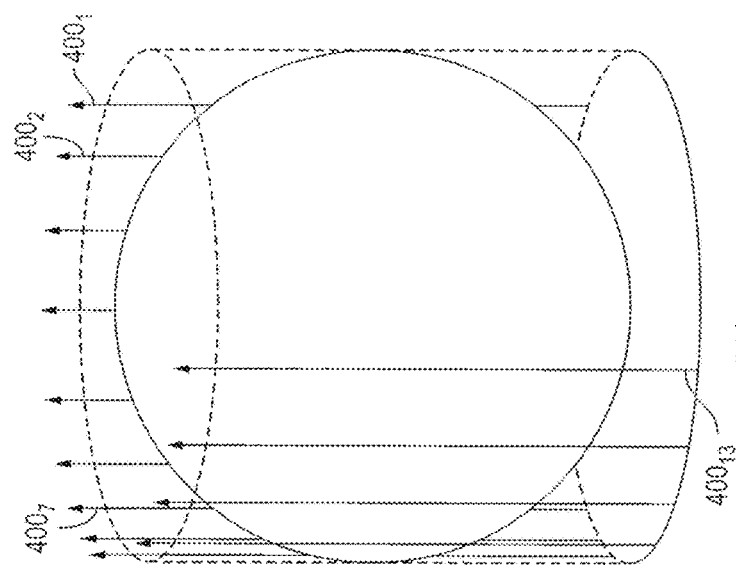

FIG. 17A shows a multitude of magnetic field inducing elements positioned around outer surface of a sphere to control the movement of magnetic particles disposed therein, in accordance with one exemplary embodiment of the present invention.

FIG. 17B is a view along the z-axis of the sphere and the field inducing elements shown in FIG. 17A.

FIG. 17C is an exemplary timing diagram of the signals applied to the magnetic field inducing elements of FIG. 17A, in accordance with one exemplary embodiment of the present invention.

Figure 17E:
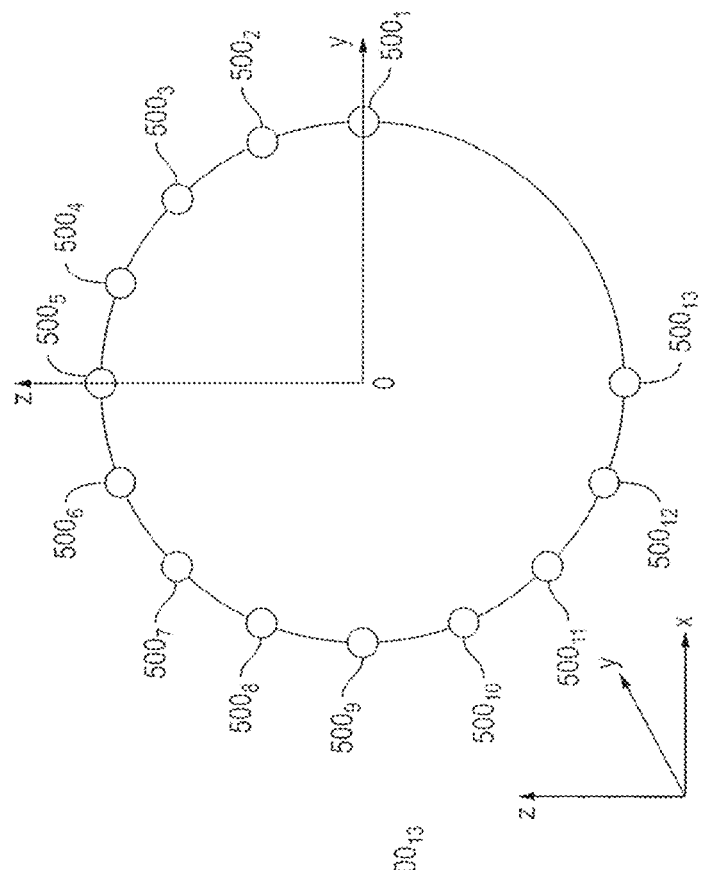
Figure 17D:
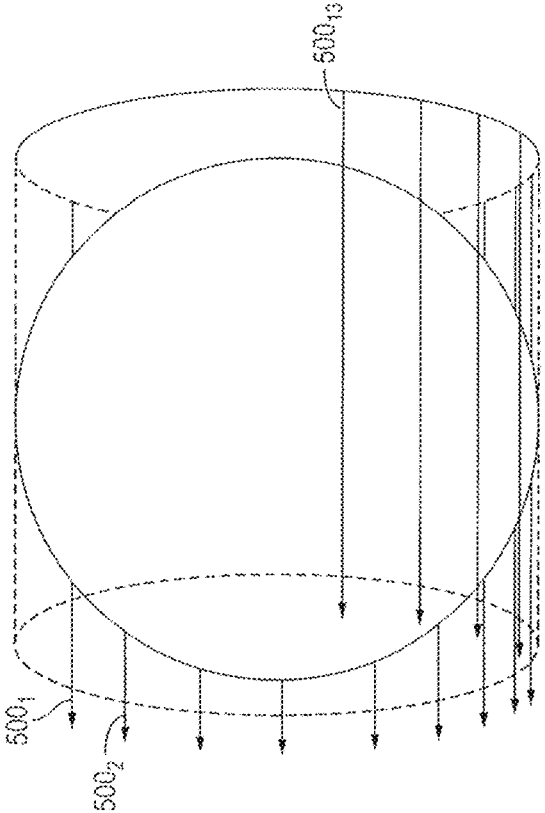

FIG. 17D shows a multitude of magnetic field inducing elements positioned along the x-axis and around the sphere of FIG. 17A to control the movement of magnetic particles disposed therein, in accordance with one embodiment of the present invention.

FIG. 17E is a view along the x-axis of the sphere and the field inducing elements shown in FIG. 17D.

Figure 17F:
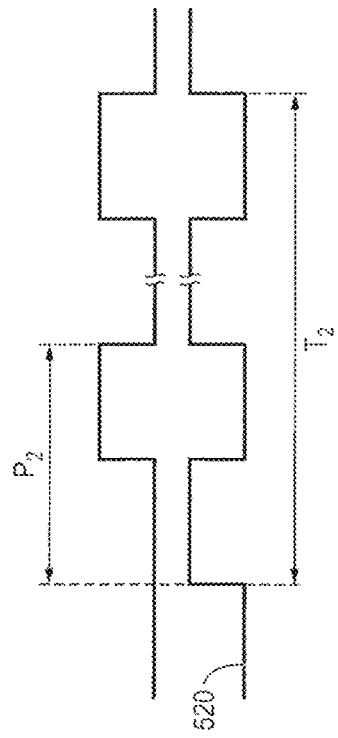

FIG. 17F is an exemplary timing diagram of the signals applied to the magnetic field inducing elements shown in FIG. 17D, in accordance with one exemplary embodiment of the present invention.

Figure 18A:
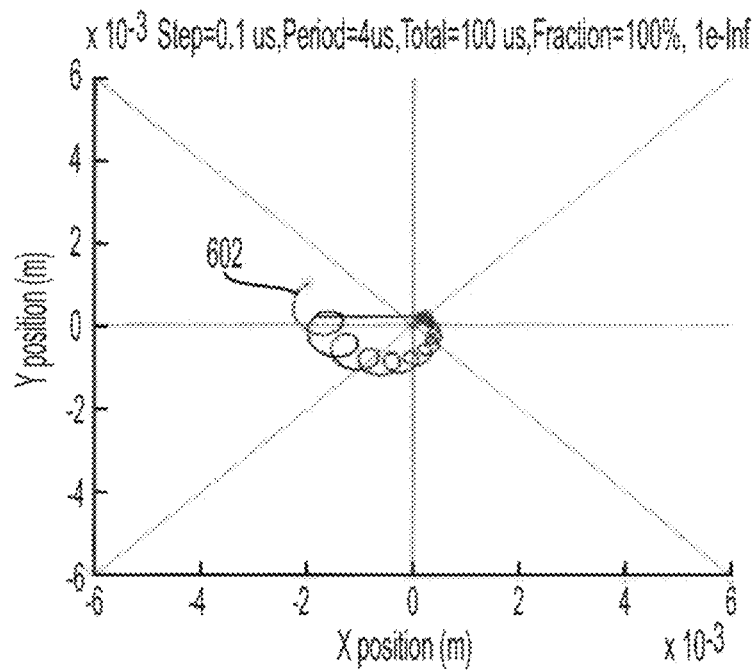

FIG. 18A shows the trajectory of magnetic particles toward the z-axis of the sphere of FIG. 17A when the particles are subjected to a number of alternating cycles of the magnetic field profiles generated by the magnetic field inducing elements of FIG. 17A.

Figure 18B:
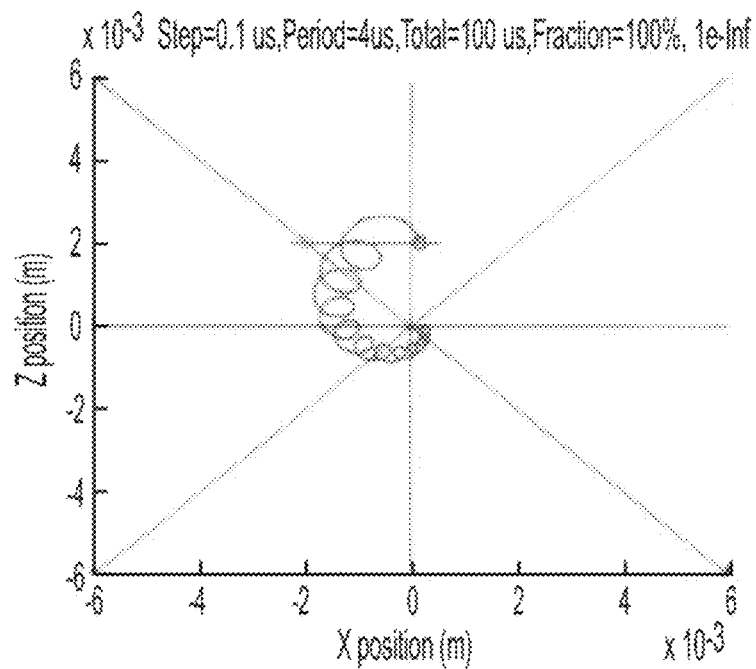

FIG. 18B, shows the trajectory of the particles toward the center of the sphere when the particles are subjected to a number of alternating cycles of the magnetic field profiles generated by the magnetic field inducing elements shown in FIGS. 17A and 17B.

Figure 19A:
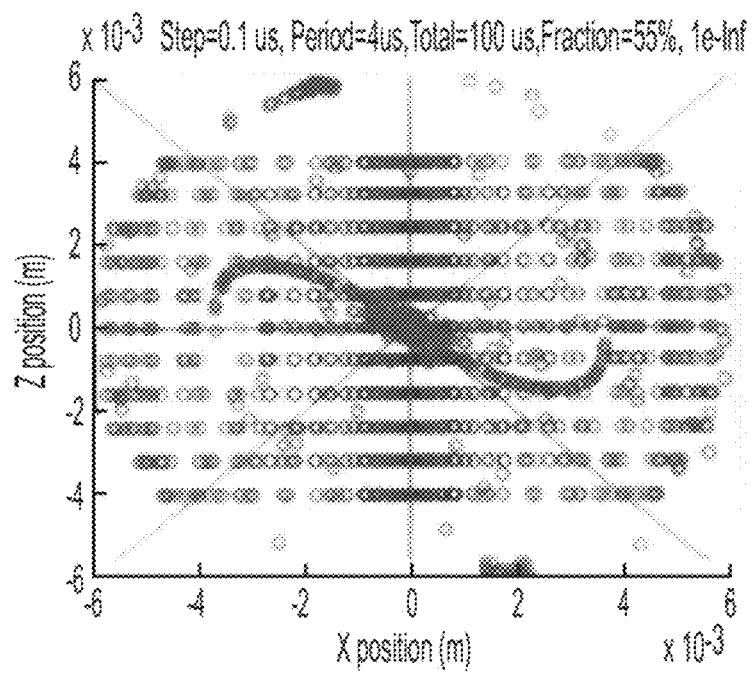
Figure 19B:
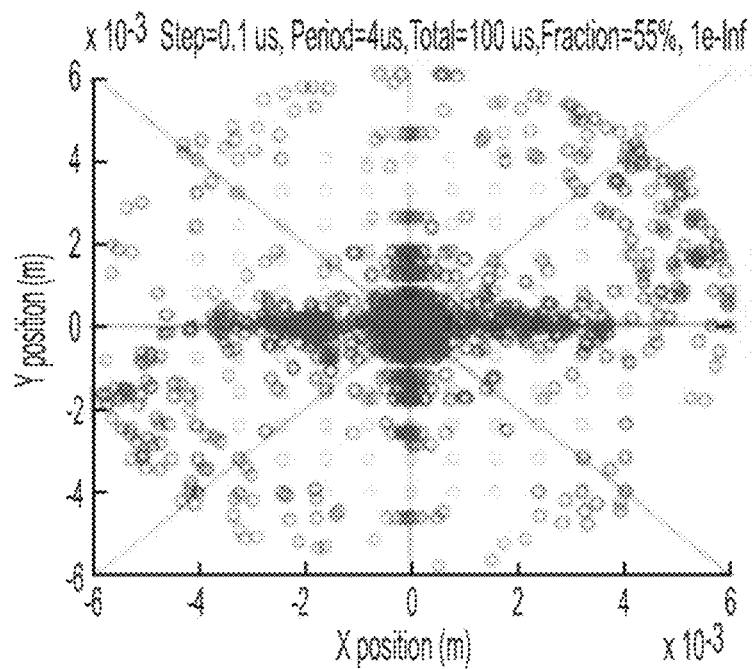

FIGS. 19A and 19B are respectively top and side views of the trajectory of particles subjected to a number of alternating cycles of the magnetic field profiles generated by the magnetic field inducing elements, as shown in FIGS. 17A and 17B.

Figure 20A:
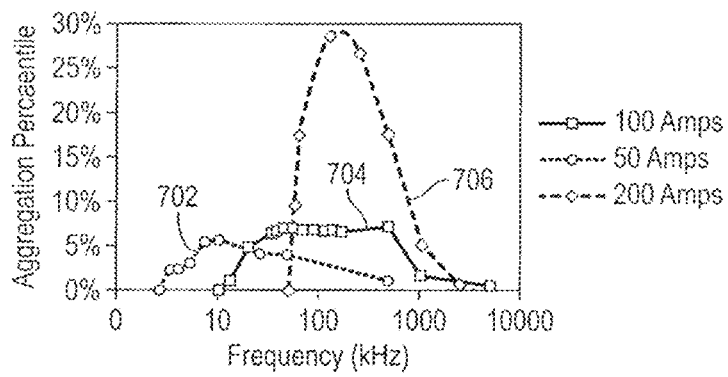

FIG. 20A shows the aggregation percentile as a function of the frequency of switching between different magnetic field profiles for various applied currents, in accordance with one exemplary embodiment of the present invention.

Figure 20B:
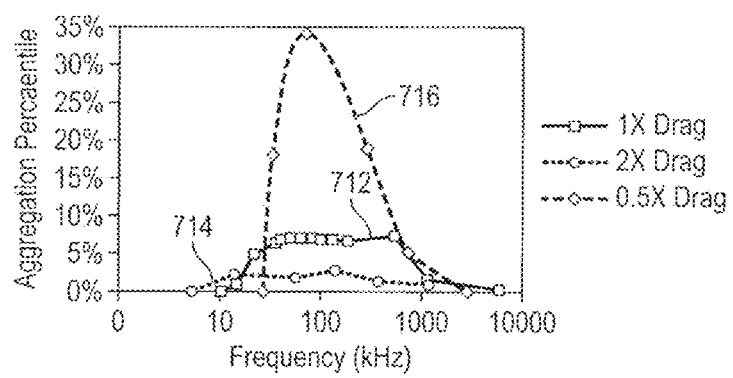

FIG. 20B shows the aggregation percentile as a function of the frequency of switching between different magnetic field profiles for various particle drag coefficients, in accordance with one exemplary embodiment of the present invention.

Figure 20C:
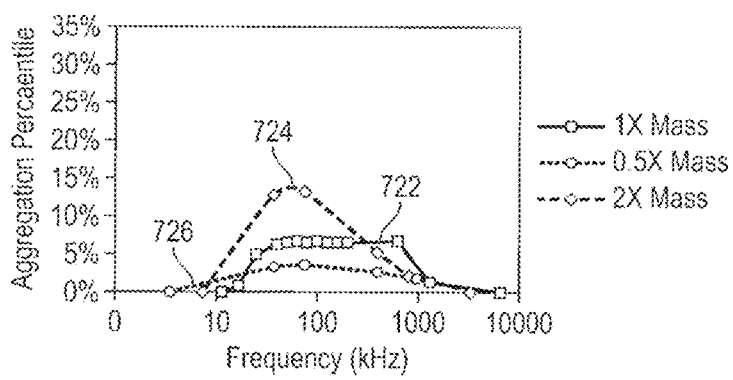

FIG. 20C shows the aggregation percentile as a function of the frequency of switching between different magnetic field profiles for various particle mass coefficients, in accordance with one exemplary embodiment of the present invention.

Figure 21:
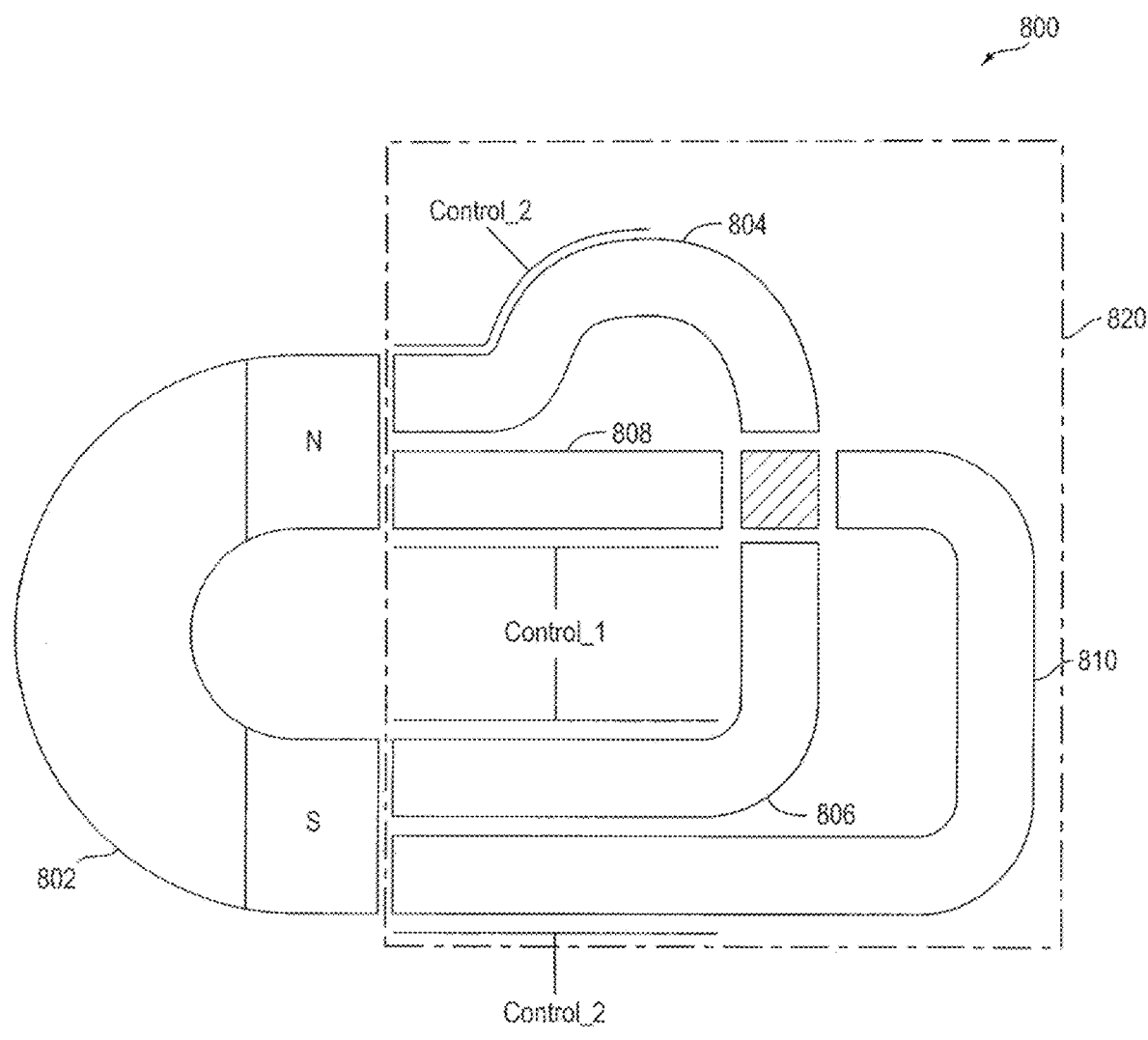

FIG. 21 is a schematic diagram of a device adapted to aggregate devices, in accordance with another exemplary embodiment of the present invention.

DETAILED DESCRIPTION OF THE INVENTION

In accordance with embodiments of the present invention, particles responsive to a magnetic or electric field are delivered and aggregated in a target region using an open loop system that does not use feedback control. Although the following description of the embodiments of the present invention is provided with reference to actuation and aggregating of particles using magnetic fields, it is understood that the embodiments of the present invention are equally applicable to actuation and aggregation of particles using electric fields.

As described further below, a device in accordance with embodiments of the present invention, is adapted to enable the controlled movement and aggregation of particles inside a living, non-living, or combination of living and non-living space. In one embodiment, the device includes a multitude of actuation blocks and is adapted to enclose a region in which the target or aggregation region is located. The actuation blocks are further adapted to operate in concert to deliver the particles to the target region. Accordingly, a device in accordance with embodiments of the present, may be used to aggregate the particles in regions that are difficult to access or to guide the particle along certain trajectories.

Actuation may include movement, or state change, such as temperature, magnetization, and orientation change. An actuation block may include one or more actuation mechanisms, such as electric, magnetic, electromagnetic, fluidic, and the like, as well as control circuitry. Communication among actuation blocks may be carried out over a wired and/or wireless communication system so as to dynamically control and program the field, magnetic or otherwise, established by the actuation blocks.

FIG. 1A shows an exemplary device 100 adapted to deliver therapeutic agents coated with magnetic particles to a predefined target position with a user's head. Device 100, which is adapted to conform to a person's head, is shown as including a multitude of actuation blocks 102. In accordance with one embodiment of the present invention, each actuation block is adapted to programmably and dynamically generate a magnetic field, in turn enabling device 100 to generate a dynamically programmable magnetic field profile configured to transport the magnetic particles inside the person's head. The magnetic particles may be attached to a therapeutic agent such as an adjuvant or cell. The temporally adjusted magnetic field profile guides the therapeutic agent to a target position to, for example, treat a disease. In another example, the magnetic particles may be attached to neural stem cells and used to treat neurodegenerative diseases. In yet another example, magnetic particles may be endocytosed by macrophages and directed toward a tumor site to treat cancer.

In the exemplary embodiment shown in FIG. 1A, each actuation block 102 is adapted to generate a magnetic field in response to, for example, one or more electrical current delivered to the actuation block. For example, in one embodiment, each actuation block 102 is shown as including a magnetic field inducing element 104 adapted to generate a magnetic field in response to an electrical current passing through the magnetic field inducing element 104. Although an actuation block is described herein as generating a magnetic field, it is understood that other embodiments of the present invention are not so limited, and that an actuation block, in accordance with embodiments of the present invention, may generate an electric field and the like.

FIG. 1B is a simplified block diagram of an exemplary actuation block 102 disposed in device 100 of FIG. 1A. Exemplary actuation block 102 is shown as including a controller 150, a magnetic field inducing element 152 and a communication unit 154. In one embodiment, controller 150 is adapted to control, among other things, the amount and duration of the current delivered to magnetic field inducing element 152. In response, magnetic field inducing element 152 generates a magnetic field. In other embodiments, when magnetic field inducing element 152 is a Ferro-magnetic material, controller 152 causes the magnetization orientation of the Ferro-magnetic material to change. In yet other embodiments, when magnetic field inducing element 152 includes permanent magnets, controller 152 is adapted to move the magnetic field inducing elements to generate the desired changes in the magnetic field profiles. Communication unit 154 is adapted to facilitate communication between the actuation blocks. In the following description of the embodiments of the present invention, magnetic field inducing elements are assumed to include conductors/wires that generate a magnetic field in response to changes in the electrical current they receive. It is understood that embodiments of the present invention are equally applicable to any other magnetic field inducing elements FIG. 1C is a simplified block diagram of a device 100 having a multitude of actuation blocks $102_j$, where j is an index varying from 1 to N, where N is an integer greater than 1. Central controller 175 of device 100 controls the various controllers 150 disposed in the actuation blocks. For example, in one embodiment, central controller 175, through local controllers 150, determines and establishes (i) the state of the local field inducing elements in each actuation block, (ii) the amount of current each magnetic field inducing element receives, (iii) the frequency of alternating between different magnetic field profiles generated by the multitude of magnetic field inducing elements 150, and the like. Central controller 175 may also facilitate communications between different actuation blocks.

FIG. 2A shows device 100 when positioned over a person's head. FIG. 2B shows a device 150 adapted to deliver therapeutic agents coated with magnetic particles to a predefined target position with a user's head, in accordance with another exemplary embodiment of the present invention. In device the varying magnetic fields are generated by rotating the inner dome 145 relative to outer dome 155. The rotation causes field inducing elements 152 positioned on inner dome 145 and field inducing elements 154 positioned on outer dome 154 to generate an alternating magnetic field profile adapted to aggregate the particles in a target location.

As is seen from FIGS. 1A and 2, in exemplary device 100 each actuation block has a triangular shape and includes one or more grooves and/or protrusions that enable that actuation block to physically mate with and engage a neighboring actuation block so as to form a mesh conforming to the exterior surface of the region on which the device is placed for the controlled delivery and aggregation of the particles. FIG. 3 shows a multitude of actuation blocks 102 coupled to one another to form device 100. In FIG. 3, the details of the actuation blocks and magnetic field inducing elements 104 are not shown for clarity. Each actuation block 102 is shown as having a triangular structure and includes protrusions and/or grooves that are used to couple that actuation block to its neighboring actuation blocks. For example, actuation block $102_1$ is shown as including three protrusions $110_1$, $110_2$, and $110_3$ positioned along its three edges that are inserted into, for example, grooves of neighboring actuation blocks $102_2$, $102_3$, and $102_4$. The conformal mesh formed by fitting the actuation blocks together contours the head's surface to minimize the separation between the particles and the actuation blocks. It is understood that in other embodiments, the actuation blocks may have hexagonal, pentagonal, rectangular, circular, octagonal, or irregular shapes.

FIG. 4 shows an exemplary actuation block 102, in accordance with another embodiment of the present invention. Actuation block 102 is shown as including 6 protrusions $130_1$, $130_2$, $130_3$, $130_4$, $130_5$, $130_6$ and three openings $140_1$, $140_2$, and $140_3$ disposed along its three sides. Opening 160 also formed within actuation block 102 is adapted to receive one or more components, such as a magnetic field inducing element 104, to generate an electric or magnetic field. Openings $140_1$, $140_2$, $140_3$, and protrusions $130_1$, $130_2$, $130_3$, $130_4$, $130_5$, and $130_6$ have the same width. Although not shown, some actuation blocks that mate with actuation block 102 may not have opening 160. In one embodiment, an actuation block mating with actuation block 102 from the left hand side may have two openings to receive protrusions $130_5$ and $130_6$, as well as a protrusion for insertion into opening $140_2$. In yet another embodiment, an actuation block mating with actuation block 102 from the left hand side may have protrusions that mate and overlap with protrusions $130_5$ and $130_6$ and inserted into opening $140_3$. It is understood that many other variations and combinations are possible.

FIG. 5 shows three actuation blocks, namely actuation blocks $102_1$, $102_2$ and $102_3$ that are mated to form a conforming mesh. In the example shown in FIG. 5, only actuation block $102_2$ is shown as having an opening 160 near its center to receive a magnetic field inducing element 104.

FIG. 6A is a perspective side view of an actuation block 102 showing more details of a protrusion 130 and its member 135 that is shaped as a hook. FIG. 6B is a perspective side view of an actuation block 102 showing more details of an opening 120 and cavity 125 formed along the length of the opening 120. As is seen from FIGS. 6A and 6B, when protrusion 130 is inserted into opening 125, hook 135 rests inside opening 125 to firmly secure the two actuation blocks. FIG. 7 shows a number of actuation blocks held together to form a conforming mesh to enclose a portion of the surface area of a spherical object 180.

As described above and further below, a device, such as device 100 shown in FIG. 1, in accordance with one embodiment of the present invention, programmably and dynamically generates and controls magnetic field profiles to direct the magnetic particles to a stable aggregation point as they experience a drag force. To explain the operation of a device, such as device 100 shown in FIG. 1, and how its multitude of actuation blocks operate in concert to direct the magnetic particles to a stable aggregation region, description is provided below with reference to the controlled movement and aggregation of particles to a target region located within a two-dimensional circular area, as well as to a target region located within the center of a spherical object.

FIG. 8A is a top view of a circular area that a device (not shown in full in FIG. 8A) in accordance with one exemplary embodiment of the present invention, may be conformed to cover to aggregate the magnetic particle positioned on the circular area to a target region near its center. Positioned within the periphery of the circular area are 13 equally-spaced straight conductors (hereinafter alternatively referred to as wires) $200_1$, $200_2$ . . . , $200_{12}$, $200_{13}$ disposed in the device that are substantially perpendicular to the surface of the circle. FIG. 8B is a perspective side view of the arrangement shown in FIG. 8A. Although only 13 wires of the device, in accordance with one exemplary embodiment, is shown in FIG. 8A, it is understood that such a device often has more wires. For example, in generating the simulation results shown in FIGS. 9A-9B, 12A and 12C-12E, nearly 200 wires were used in the device in the arrangement shown in FIGS. 8A and 8B.

Assume that during time period $T_1$ a current of one Ampere is passed through each of wires $200_1$, $200_2$ . . . $200_9$, collectively referred to herein as the first group of wires. FIG. 9A is a computer generated quiver plot of the magnetic field created within area 250 of the circular area in response to passing the currents through nearly 200 such wires positioned between wires $200_1$ and $200_9$. The direction of the currents through the wires does not change the field profile, as long as all the currents are all in the same direction. The direction of the arrow at each position of the quiver plot represents the direction of the force that a magnetic particle experiences at that position. The length of the arrow at each location is scaled to substantially represent the magnitude of the force at that location. It is seen that the field profile creates a saddle point near the center region of the circle. It is also seen that particles are guided to the left and right most points of the circle's boundary at x-y coordinates (−6, 0) and (6, 0).

Assume that during time period $T_2$ a current of one Ampere is passed through each of wires $200_5$, $200_6$ . . . $200_{13}$, collectively referred to herein as the second group of wires. FIG. 9B shows a computer generated quiver plot of the magnetic field created within area 250 of the circular area in response to passing the currents through nearly 200 such wires positioned between wires $200_5$ and $200_{13}$. The direction of the currents through the wires does not change the field profile, as long as all the currents are all in the same direction. As in FIG. 9A, the direction of the arrow at each position of the quiver plot represents the direction of the force that a magnetic particle experiences at that position, and the length of the arrow at each location is scaled to substantially represent the magnitude of the force at that location. It is seen that the field profile creates a saddle point near the center region of the circle. It is also seen that particles are guided to the top and bottom of the center points of the circle's boundary at x-y coordinates (0, 6) and (0, −6).

In accordance with embodiments of the present invention, by switching the currents passing through the first and second group of wires in order to alternate between the two magnetic field profiles shown in FIGS. 9A and 9B, a stable region is created near the center of the circle in which particles are aggregated. FIG. 10A shows the trajectory of particles—placed initially at point A—in response to alternating between the two magnetic field profiles shown in FIGS. 9A and 9B. As is seen, in response to the alternating magnetic field profiles, the particles are directed toward the center of the circle. FIG. 10B is an expanded view of a portion of the region of FIG. 10A showing the particles' trajectory toward the center of the simulation area as the magnetic field profile alternates between those shown in FIGS. 9A and 9B.

Although in the exemplary embodiment shown in FIGS. 8A and 8B, conductors $200_i$ (i is an index ranging from 1 to 13 in FIGS. 8A and 8b) are shown as being perpendicular to the surface of the circular area, it is understood that in other embodiments, conductors $200_i$ may not be perpendicular to the surface of the circular region. Furthermore, although in the exemplary embodiments shown in FIGS. 8A and 8B, the first group of conductors $200_1$, $200_2$ . . . $200_9$ are shown as being parallel to the second group of conductors $200_5$, $200_6$ . . . $200_{13}$, it is understood that in other embodiments, the two groups of conductors are not parallel to one another. In yet other embodiments, neither of the two groups of wires is perpendicular to the surface of the circular area and the two groups of wires are not parallel to one another. Furthermore, although the above example is shown with reference to a circular area for simplicity, it is understood that the above embodiments of the present invention may be equally applied to any regularly or irregularly shaped plane or volume in space.

In some embodiments, a single set of wires may be used and then rotated in a clockwise or counter clockwise manner so as to be positioned at a different location to create alternating magnetic field profiles. For example, in the arrangement shown in FIGS. 11A and 11B, during time period $T_1$, wires $200_1$, $200_2$ . . . $200_9$ are shown as being perpendicular to a top half of the periphery of the circular area. At time $T_2$, the wires are shown as having been rotated counterclockwise by 90 degrees so as to be perpendicular to a left half of the periphery of the circular area. By rotating the wires as shown, the alternating magnetic field profiles shown in FIGS. 9A and 9B are achieved thereby directing and aggregating the particles near the center region, as shown in FIGS. 10A and 10B.

FIGS. 12A and 12C-12E show the effect of the switching speed between the magnetic field profiles (i.e., frequency of the change in the magnetic field profiles) shown in FIGS. 9A-9B on the speed distribution of the particles positioned within the simulation area 250 of FIG. 8A when one ampere of current is passed for a period of 2 µsec in an alternating manner between the first and second groups of wires for a total time interval of 50 µsec (i.e., 25 clock cycles) Alex, please check.

Waveform 300 of FIG. 12B is the timing diagram of the current signal passed through each wire of the first group of wires, and waveform 302 of FIG. 12B is the timing diagram of the current signal passed through each wire of the second group of wires. As is seen from FIGS. 12A and 12B, during each 1 µsec of a clock having a period of 2 µsec, a current is supplied to the wires in a different one of the wire groups. Although in FIG. 12B, the signals applied to the two groups of wires are shown as being non-overlapping signals, it is understood that in other embodiment, the signals may overlap. Furthermore, although in the above example, the same amount of current is supplied to the wires in each wire group, in other embodiments, different currents may be applied to different wire groups as well as to the wires within each group. Because in FIG. 2B, the current is switched between the two wire groups every 1 µsec, it is understood that the frequency of the change in the magnetic field profile is 1 MHz.

The heat map shown on the right of the FIG. 12 A provides the speed in millimeter per second of the particles toward the center region. As is seen from FIG. 12A, the region near the center experiences no field (i.e., speed of zero) and thus provides a stable aggregation region for the particles. FIGS. 12C, 12D and 12E show the speed distribution of the particles when the period of current signals (see FIG. 12B) is respectively set to 4 µsec, 6 µsec, and 8 µsec, thereby reflecting the change in the speed distribution and aggregation of the particles in response to change in the frequency of alternating between the different magnetic field profiles.

In accordance with embodiments of the present invention, the size of the area that is subject to the magnetic field, the size of the aggregation area, and the speed of the particles towards the aggregation point may be controlled by varying the value of the electrical current supplied to each wire, the switching speed between the wire groups, or the speed at which the wire groups are rotated, the total number of wires in each group, the relative positions of the wires, the fluid properties through which the particles move, as well as the magnetic susceptibility of the medium through which the particles move.

As was described above, in some embodiments, one or more sets of wires may be rotated in, for example, clockwise, counter clockwise, or any other direction to generate alternating magnetic field profiles. For example, the 9 wires shown in FIG. 11A may be rotated 10 times each time at an angle of 9° in a counter clockwise direction. Accordingly, after 10 such rotations the wire arrangement shown in FIG. 11A is transformed to that shown in FIG. 11B. FIG. 13A shows the wire positions after one 9° rotation of the wires shown in FIG. 11A. FIG. 13B shows the wire positions after one 9° rotation of the wires shown in FIG. 13A. After each such rotation, a current is passed through the wires to generate a corresponding magnetic field profile. Accordingly, in this example, 10 different magnetic field profiles are dynamically created to generate an aggregation area larger than those associated with FIGS. 12A and 12C-12D.

Figure 14A:
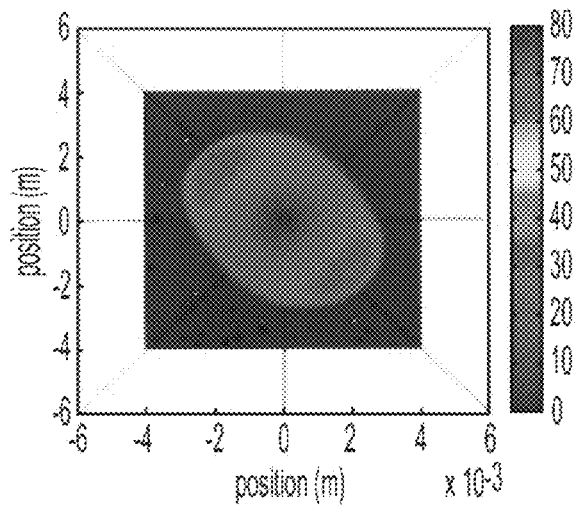
Figure 14B:
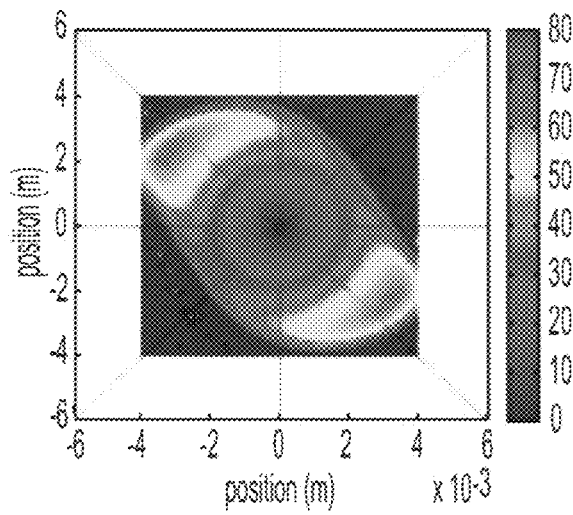
Figure 14C:
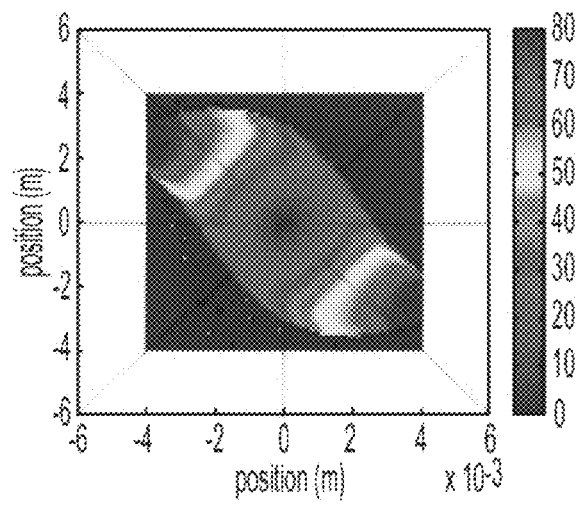
Figure 14D:
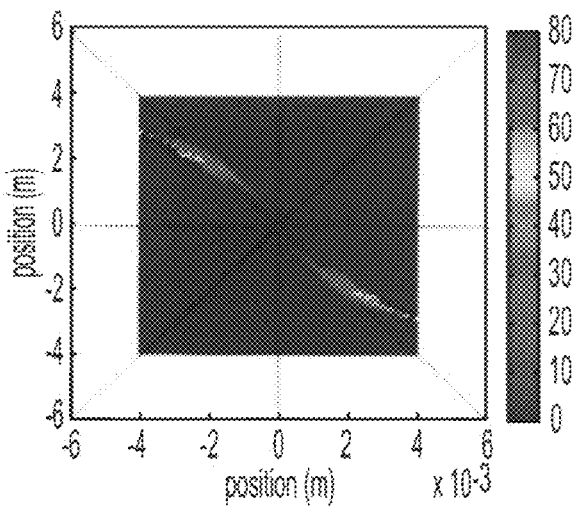

FIG. 14A shows the speed distribution of the particles within the simulation area 250 of FIG. 13A when one ampere of current is supplied to each wire for a period 20 µsec after each ten 9° rotation of the wires. The heat map shown on the right of the FIG. 12 A provides the speed in millimeter per second of the particles toward the center region. As is seen, the size of the aggregation area is larger in FIG. 14A relative to that in FIG. 12A. It is also seen from FIG. 14A that the region near the center experiences no field (i.e., speed of zero) and thus provides a stable aggregation region for the particles. FIGS. 14B, 14C and 14D show the speed distribution of the particles when the periods of applied current signals are respectively set to 60 µsec, 80 µsec, and 100 µsec. Accordingly, as is seen from FIGS. 14A-14D, by changing the frequency of the change in the magnetic field profiles, the particle aggregation may be controlled. Although in the examples shown above with respect to FIGS. 13A-13B and 14A-14D, the ten magnetic profiles are generated by performing ten 9° rotations of the same group of wires and applying currents in an alternating manner during each such rotation, it is understood that in other embodiments, the different magnetic field profiles may be achieved without rotating the wires and by switching currents in an alternating manner through wires already positioned along the periphery of the circular area in the same fashion as described above in connection with FIG. 8A.

In the example shown with reference to FIGS. 8A-8B, 9A-9B and 10A-10B, each of the first and second group of wires is shown as including 9 wires, it is understood however, that in other embodiments, more than 9 wires may be disposed in each wire group. Furthermore, in other embodiments, any integer number N of wire groups, each having any integer number M of wires, may be used to create field profiles that may be alternated, in accordance with embodiments of the present invention, to direct and aggregate particles near a target location. It is also understood that the wire groups may be arranged along other positions. For example, FIG. 15 shows four wire sets each having seven wires positioned along the periphery of the circular area. Wires $250_1, 250_2 \ldots 250_6, 250_7$ form a first group of wires; wires $250_7, 250_8 \ldots 250_{13}, 250_{14}$ form a second group of wires; wires $250_{14}, 250_{15} \ldots 250_{20}, 250_{21}$ form a third group of wires; and wires $250_{21}, 250_{22} \ldots 250_{26}, 250_1$ form a fourth group of wires. By switching currents through these four wire sets during different time periods to generate different magnetic field profiles, particles positioned within the circle's area are guided and aggregated near the center of the circle.

Controlled movement of particles, in accordance with embodiments of the present invention, faces negligible impact from Brownian motion. FIG. 16A shows the speed distribution of the particles at room temperature within the simulation area 250 of FIG. 13A when one ampere of current is passed for a period 60 μsec after each of ten 9° rotation of the wires. FIGS. 16B, 16C and 16D respectively show the speed distribution of the particles under similar operating conditions as in FIG. 16A except that in FIGS. 16B, 16C and 16D, the temperatures have been increased to such degrees that the Brownian motions are increased by $10^{10}$, $10^{11}$ and $10^{12}$ respectively. As is seen from FIGS. 16B-16D, only when the temperature is raised to such high degrees, does the speed distributions change. Although not shown, computer simulations shown no noticeable change in speed distribution of the particle due to Brownian motion in response to variations in ambient temperature.

Controlled movement and aggregation of particles in a three-dimensional space is described and shown below. FIG. 17A shows various magnetic field inducing elements $400_i$, where i is an integer index greater than one, positioned around outer surface of a sphere 400 to direct and aggregate particles disposed in the sphere toward the sphere's center, in accordance with one exemplary embodiment of the present invention. To achieve this, in accordance with one embodiment, at least a first pair of magnetic field profiles are generated within the sphere along the x-y direction in an alternating manner, and at least a second pair of magnetic field profiles are generated within the sphere along the x-z direction in an alternating manner. In the example shown in FIG. 17A, the first pair of magnetic field profiles are generated by passing electrical currents through a multitude of wires that are substantially perpendicular to the x-y plane. The second pair of magnetic field profiles are also generated by passing electrical currents through a multitude of wires that are substantially perpendicular to the x-z plane.

In the example shown in FIG. 17A, a first set of wires, namely wires $400_1, 400_2 \ldots 400_{13}$, are positioned perpendicularly to the x-y plane such that the radial angle between each adjacent pair of wires in the x-y plane is 22.5°. FIG. 17B is a top view of a cross-section of an x-y plane and sphere 400 at the sphere's center. As is seen from FIG. 17B, the wires cover 270 degrees in the x-y plane such that the radial angle θ between each adjacent pair of wires is 22.5° in this example. As described further below, wires $400_1, 400_2 \ldots 400_9$ form a first group of wires within the first set of wires. As is seen, the first group of wires collectively cover 180° between the two points defined by the cross sections of wires $400_1$ and $400_9$ and the x-y plane. Wires $400_5, 400_6 \ldots 400_{13}$ form a second group of wires within the first set of wires. As is seen, the second group of wires collectively cover 180° between the two points defined by the cross sections of wires $400_5$ and $400_{13}$ and the x-y plane, as shown.

Also disposed along the outer surface of sphere 400 are a second set of wires, namely wires $500_1, 500_2 \ldots 500_{13}$, shown in FIG. 17D as being perpendicular to the y-z plane such that the radial angle between each pair of adjacent wires in the y-z plane is 22.5°. FIG. 17E is a top view of a cross-section of a y-z plane and sphere 400 at the sphere's center. As is seen from FIG. 17E, the wires cover 270 degrees in the y-z plane such that the radial angle θ between each adjacent pair of wires is 22.5° in this example. As described further below, wires $500_1, 500_2 \ldots 500_9$ form a first group of wires within the second set of wires. As is seen, the first group of wires collectively cover 180° between the two points defined by the cross sections of the y-z plane and wires $500_1$ and $500_9$. Wires $500_5, 500_6 \ldots 500_{13}$ form a second group of wires within the second set of wires. As is seen, the second group of wires collectively cover 180° between the two points defined by the cross sections of the y-z plane and wires $500_5$ and $500_{13}$.

Although in the above example, only 2 sets of wires are shown as being disposed around the sphere, it is understood that embodiments of the present invention are not so limited and that any number of sets of wires may be used. Although in the above example, each set is shown as including 13 wires, it is understood that in other embodiments fewer or more than 13 wires may be used in each set. Although in the above example each set is shown as including 2 groups of wires overlapping by 90° rotation and covering 270° of the cross-section of a plane of the sphere and the wires, it is understood that in other embodiments, the wires in each set may be divided into more than two groups, and the overlapping area between each successive groups may be more or less than 90°, and the total angular area covered by each wire set may be more or less than 270°. Furthermore, although in the above embodiments, wire sets $400_i$ (where i is an index varying from 1 to 13 in the examples shown in FIGS. 17A-17D), and $500_i$ are shown as being physically distinct wires, it is understood that in yet other embodiments wire sets $400_i$ and $500_i$ may be the same set of wires that can be rotated back and forth by 90° to arrive at the wire orientations shown in FIGS. 17A and 17C. Moreover, although the wires in the different groups of the same set are shown as being different wires, it is understood that in other embodiments, the same set of wires may be repositioned to achieve the same effect. For example, referring to FIG. 17B, after passing current through the wires $400_1 \ldots 400_9$, the wires may be moved by 90° in a counter clockwise fashion so as to occupy positions shown in FIG. 17B as $400_5 \ldots 400_{13}$. Yet in other embodiments, the same effect may be achieved by maintaining the wire in a fixed orientation and rotating the sphere by 90° relative to the wires. Furthermore, instead of using two sets of wires, the sphere may be rotated with respect to the same set of wires.

Furthermore, although in the above embodiments, the first and second set of wires are shown as being perpendicular to one another, it is understood that in other embodiments, the first and second set of wires may not be perpendicular to one another. Furthermore, although in the above embodiments, the first and second group of wires in each set are shown as being parallel to one another, in other embodiments, the first and second set of group of wires disposed in each wires may not be parallel to one another.

To direct particles to a target region near the center of sphere 600, in accordance with embodiments of the present invention, during a first time interval $T_1$, a current is passed through the first and second groups of wires of the first set of wires $400_i$ in an alternating manner for K cycles, where K is an integer greater than one, as shown in FIG. 17C. Waveforms 410 and 420 are exemplary timing diagrams of current signals applied respectively to the first and second groups of wires disposed in wire set $400_i$. As is seen from waveform 410 of FIG. 17B, during one half (e.g. high cycles or high values) of each period $P_1$, a current is passed through wires $400_1 \ldots 400_9$ forming the first group of the first wire set $400_i$, and during the other half (e.g., low cycles or low values) of each period $P_1$ as shown in waveform 420 of FIG. 17B, a current is passed through wires $400_5 \ldots 400_{13}$ forming the second group of the first wire set $400_i$. After the expiration of time interval $T_1$ (K cycles of period $P_1$) when the current through the first wire set $400_i$ is turned off, during a second time interval $T_2$, a current is passed through the first and second groups of wires of the second set of wires $500_i$ in an alternating manner for N cycles, where N is an integer greater than one, as shown in FIG. 17F. Waveforms 510 and 520 are exemplary timing diagrams of current signals applied to the first and second groups of wires disposed in wire set $500_u$. As is seen from FIG. 17F, during one half (e.g., high cycles) of each period $P_2$, a current is passed through wires $500_1 \ldots 500_9$ forming the first group of the second wires set $500_i$, and during the other half of each period $P_2$, a current is passed through wires $500_5 \ldots 500_{13}$ forming the second group of the second wire set $500_i$. Although in FIG. 17B, the signals applied to the two groups of wires are shown as being non-overlapping signals, it is understood that in other embodiment, the signals may overlap. Furthermore, although in the above example, the same amount of current is supplied to the wires in each wire group, in other embodiments, different currents may be applied to different wire sets, to different wire groups within a wire set, as well as to different wires within each group.

FIG. 18A shows the spiral trajectory of particles from their initial position near region 602 in the x-y plane toward the z-axis of the sphere when the particles are subjected to a number of alternating cycles of the first and second groups of the first set of wires $400_i$, as shown in FIG. 17C, except that in the experimental simulation performed in FIG. 18A, each group of wires is assumed to have nearly 200 wires When viewed along the z-axis, the particles form a column around the central axis of the sphere in the z direction. FIG. 18B, shows the spiral trajectory of the particles in the x-z plane (from their final positions in FIG. 18A following the expiration of time $T_1$) after the particles are subjected to a number of alternating cycles of the first and second groups of the second set of wires $500_i$, as shown in FIG. 17F.

FIGS. 19A and 19B are respectively top (x-y plane) and side views (x-z plane) of a multitude of particles (shown in red color) assumed to initially occupy a cubic area in sphere 600. After a number of alternating cycles of the magnetic fields generated by the first and second groups of wires $400_i$, the particles (shown in blue color) are shown as forming a cylindrical shaped column around the central axis of the sphere along the z-axis. After a number of alternating cycles of the magnetic fields generated by the first and second groups of wires $500_i$, the particles (shown in green color) aggregate near the center of the sphere. Computer simulations show that 55% of the particles aggregate near the center of the sphere when one ampere of current is passed through each wire group for a duration of 2 μsec and when each of the time intervals $T_1$ and $T_2$ is set to 50 μsec.

As described in detailed above, in accordance with embodiments of the present invention, by dynamically changing a magnetic field profile, particles exposed thereto are directed and aggregated near a target region. The magnetic field profile may be changed by changing a number of variables, such as by changing the time duration (period) of various magnetic fields and thus the frequency of change in the magnetic field profiles, or by changing the total time interval during which particles are exposed to the changing magnetic fields, or by changing the amount of current supplied to wires generating the magnetic fields, and the like. Furthermore, referring to FIGS. 17A and 17B, by changing the number of wire sets, or the number of groups in each wire sets, or the number of wires in each group, or the size of the angular overlap between the neighboring groups of each wire set and the total angular area that they cover (shown as 270°) in the above embodiments, and the like, the fraction of the particles that are aggregated near the target region may be varied.

An actuation device in accordance with embodiments of the present invention, is thus adapted to control both the aggregation of the magnetic particles as well as the fraction of the particles that are so aggregated using a number of variables. Plots 702, 704 and 706 of FIG. 20A respectively show the aggregation percentile as a function of the frequency of switching between different magnetic field profiles when currents of 50 amps, 100 amps, and 200 amps are supplied to wires creating dynamically changing magnetic field profiles, as shown for example with reference to FIG. 17A. As is seen by comparing these Figures, the aggregation percentile, i.e., the percentage of particles that are aggregated near the target region, has the highest value when the current supplied to the wires has the highest shown value.

Plots 712 of FIG. 20B shows the aggregation percentile as a function of the frequency of switching between different magnetic field profiles for a currents of 100 amps, when the drag coefficient of the magnetic particles is assumed to have a normalized value of 1. Plots 714 shows the aggregation percentile under the same conditions as in plot 712 except that in plot 714 the drag coefficient of the particles is assumed to have a value twice that shown in plot 712. Plots 716 shows the aggregation percentile under the same conditions as in plot 712 except that in plot 716 the drag coefficient of the particles is assumed to have a value equal to one half of that shown in plot 712. As is seen by comparing these Figures, the aggregation percentile has the highest value when the particle drag coefficient has the lowest shown value.

Plots 722 of FIG. 20B shows the aggregation percentile as a function of the frequency of switching between different magnetic field profiles for a currents of 100 amps, when the mass of the magnetic particles is assumed to have a normalized value of 1. Plots 724 shows the aggregation percentile under the same conditions as in plot 722 except that in plot 724, the mass of the particles is assumed to have a value twice that shown in plot 722. Plots 726 shows the aggregation percentile under the same conditions as in plot 722 except that in plot 726, the particle mass is assumed to have a value equal to one half of that shown in plot 722. As is seen by comparing these Figures, the aggregation percentile has the highest value when the mass has the lowest shown value.

FIG. 21 is a schematic diagram of a device adapted to aggregate devices, in accordance with another exemplary embodiment of the present invention. Device 800 is shown as including a permanent magnet 802 and magnetic field inducing component 820 that is shown as including elements 804, 806, 808 and 810. Each of elements 804, 806, 808 and 810 includes materials such as Ferro-magnetic that change their magnetization orientation in response to an external signal, which may be electrical, optical or electro-optical. By selectively and varying signal Control_1 applied to elements 806, 808, and signal Control_2 applied to elements 804, 810, the magnetization orientation and thus the magnetic field profile generated by magnetic field inducing component 820 is adapted to vary in region 850 thereby enabling particles disposed in region 250 to aggregate to a desired target location.

The above embodiments of the present invention are illustrative and not limitative. The embodiments of the present invention are not limited by the manner in which force fields, magnetic or otherwise, are generated; nor are they limited by the manner in which such force fields are varied to aggregate particles, or the frequency of the change in the magnetic field profiles. The above embodiments of the present invention are not limited by the number of wires that may be used in a magnetic field inducing elements to generate a magnetic field, nor are they limited by the amount of current or the duration of such currents. Other modifications and variations will be apparent to those skilled in the art and are intended to fall within the scope of the appended claims.

What is claimed is:

1. A method of aggregating particles in a three-dimensional space, the method comprising:
    generating at least a first magnetic field during a first time interval; and
    generating at least a second magnetic field during a second time interval thereby causing the particles exposed to the at least first and second magnetic fields to aggregate to a target region in response to a change from the at least first magnetic field to the at least second magnetic field, wherein said at least first and second magnetic fields are generated in response either to moving permanent magnets or to changes in magnetization orientation of a Ferro-magnetic material.

2. The method of claim 1 wherein said first and second time intervals are non-overlapping time intervals.

3. A method of aggregating particles in a three-dimensional space, the method comprising:
    generating at least a first magnetic field during a first time interval;
    generating at least a second magnetic field during a second time interval thereby causing the particles exposed to the at least first and second magnetic fields to aggregate to a target region in response to a change from the at least first magnetic field to the at least second magnetic field;
    switching between the at least first and second magnetic fields for a plurality of cycles thereby to aggregate the particles in the target region, wherein at least a portion of said first and second time intervals occur during N cycles of a clock signal, wherein N is an integer greater than one.

4. The method of claim 3 wherein the portion of the first time interval is defined by N high values of the clock and wherein the portion of said second time interval is defined by N low values of the clock.

5. The method of claim 3 further comprising:
    varying a frequency of the switching between the at least first and second magnetic fields.

6. The method of claim 5 wherein said frequency is selected in accordance with a friction coefficient of the particles.

7. The method of claim 5 wherein said frequency is selected in accordance with a drag coefficient of the particles.

8. The method of claim 5 wherein said frequency is selected in accordance with a mass of the particles.

9. A method of aggregating particles in a three-dimensional space, the method comprising:
    generating at least a first magnetic field during a first time interval;
    generating at least a second magnetic field during a second time interval thereby causing the particles exposed to the at least first and second magnetic fields to aggregate to a target region in response to a change from the at least first magnetic field to the at least second magnetic field, The method of claim 1 wherein said at least first magnetic field is generated by passing a first current through a first plurality of conductors during the first time interval and said at least second magnetic field is generated by passing a second current through a second plurality of conductors during the second time interval;
    varying the first current and varying the second current.

10. The method of claim 9 wherein said second plurality of conductors are substantially parallel to said first plurality of conductors.

11. The method of claim 9 wherein at least a subset of the first plurality of conductors are disposed in the second plurality of conductors.

12. The method of claim 9 wherein said first current is equal to said second current.

13. The method of claim 9 wherein said second plurality of conductors are formed by rotating the first plurality of conductors.

14. A method of aggregating particles in a three-dimensional space, the method comprising:
    generating at least a first magnetic field during a first time interval;
    generating at least a second magnetic field during a second time interval thereby causing the particles exposed to the at least first and second magnetic fields to aggregate to a target region in response to a change from the at least first magnetic field to the at least second magnetic field; and
    generating the at least first and second magnetic fields using an open loop system.

15. A method of aggregating particles in a three-dimensional space, the method comprising:
    generating at least a first magnetic field during a first time interval; and
    generating at least a second magnetic field during a second time interval thereby causing the particles exposed to the at least first and second magnetic fields to aggregate to a target region in response to a change from the at least first magnetic field to the at least second magnetic field The method of claim 1 wherein said first time interval is substantially equal to said second time interval.

16. A method of aggregating particles in a three-dimensional space, the method comprising:
    generating at least a first magnetic field during a first time interval; and
    generating at least a second magnetic field during a second time interval thereby causing the particles exposed to the at least first and second magnetic fields to aggregate to a target region in response to a change from the at least first magnetic field to the at least second magnetic field wherein said at least first and second magnetic fields are generated by a plurality of magnetic field generating components adapted to mate with one another to form a mesh conforming to contours of a surface enclosing a region in which the particles are disposed.

17. A device adapted to aggregate particles in a three-dimensional space, the device being dynamically programmable to:
generate at least a first magnetic field during a first time interval;
generate at least a second magnetic field during a second time interval thereby to cause the particles to aggregate to a target region in response to a change from the at least first magnetic field to the at least second magnetic field; said device comprising:
at least one permanent magnet and a controller adapted to move the at least one permanent magnet to generate the at least first and second magnetic fields.

18. The device of claim 17 wherein said first and second time intervals are non-overlapping time intervals.

19. The device of claim of claim 17 wherein the device further comprises a controller adapted to vary a frequency of switching between the at least first and second magnetic fields.

20. The device of claim 19 wherein the controller is further adapted to select the frequency of switching in accordance with a friction coefficient of the particles.

21. The device of claim 19 wherein the controller is further adapted to select the frequency of switching in accordance with a drag coefficient of the particles.

22. The device of claim 19 wherein the controller is adapted to select the frequency of switching in accordance with a mass of the particles.

23. A device adapted to aggregate particles in a three-dimensional space, the device being dynamically programmable to:
generate at least a first magnetic field during a first time interval;
generate at least a second magnetic field during a second time interval thereby to cause the particles to aggregate to a target region in response to a change from the at least first magnetic field to the at least second magnetic field;
wherein the device is further dynamically programmable to switch between the at least first and second magnetic fields for a plurality of cycles thereby to aggregate the particles in the target region, wherein at least a portion of said first and second time intervals occur during N cycles of a clock signal.

24. The device of claim 23 wherein the portion of the first time interval is defined by N high values of the clock and wherein the portion of said second time interval is defined by N low values of the clock.

25. A device adapted to aggregate particles in a three-dimensional space, the device being dynamically programmable to:
generate at least a first magnetic field during a first time interval;
generate at least a second magnetic field during a second time interval thereby to cause the particles to aggregate to a target region in response to a change from the at least first magnetic field to the at least second magnetic field, wherein said device comprises:
a first plurality of conductors adapted to receive a first current during the first time interval to generate the at least first magnetic field; [[and]] a second plurality of conductors adapted to receive a second current during the second time interval to generate the at least second magnetic field and a controller adapted to vary the first and second currents.

26. The device of claim 25 wherein said second plurality of conductors are substantially parallel to said first plurality of conductors.

27. The device of claim 25 wherein at least a subset of the first plurality of conductors are disposed in the second plurality of conductors.

28. The device of claim 25 wherein said first current is equal to second current.

29. The device of claim 25 wherein said second plurality of conductors are formed by rotating the first plurality of conductors.

30. A device adapted to aggregate particles in a three-dimensional space, the device being dynamically programmable to:
generate at least a first magnetic field during a first time interval;
generate at least a second magnetic field during a second time interval thereby to cause the particles to aggregate to a target region in response to a change from the at least first magnetic field to the at least second magnetic field, wherein said device is an open loop device.

31. A device adapted to aggregate particles in a three-dimensional space, the device being dynamically programmable to:
generate at least a first magnetic field during a first time interval;
generate at least a second magnetic field during a second time interval thereby to cause the particles to aggregate to a target region in response to a change from the at least first magnetic field to the at least second magnetic field, wherein said first time interval is substantially equal to said second time interval.

32. A device adapted to aggregate particles in a three-dimensional space, the device being dynamically programmable to:
generate at least a first magnetic field during a first time interval;
generate at least a second magnetic field during a second time interval thereby to cause the particles to aggregate to a target region in response to a change from the at least first magnetic field to the at least second magnetic field The device of claim 21 wherein the device comprises a plurality of magnetic field generating components adapted to mate with one another to form a mesh conforming to contours of a surface enclosing a region in which the particles are disposed.

33. A device adapted to aggregate particles in a three-dimensional space, the device being dynamically programmable to:
generate at least a first magnetic field during a first time interval;
generate at least a second magnetic field during a second time interval thereby to cause the particles to aggregate to a target region in response to a change from the at least first magnetic field to the at least second magnetic field, said device comprising:
a Ferro-magnetic material; and
a controller adapted to change magnetization orientation of the Ferro- magnetic material thereby to generate the at least first and second magnetic fields.

* * * * *